US008603595B2

(12) United States Patent
Kawakami et al.

(10) Patent No.: US 8,603,595 B2
(45) Date of Patent: Dec. 10, 2013

(54) LIQUID CRYSTALLINE COMPOUND, LIQUID CRYSTAL COMPOSITION, LIQUID CRYSTAL ELEMENT, AND LIQUID CRYSTAL DISPLAY DEVICE

(75) Inventors: Sachiko Kawakami, Kanagawa (JP); Yuko Kawata, Kanagawa (JP); Momoko Kato, Kanagawa (JP); Tetsuji Ishitani, Kanagawa (JP); Tomohiro Tamura, Okinawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 13/358,740

(22) Filed: Jan. 26, 2012

(65) Prior Publication Data
US 2012/0194775 A1    Aug. 2, 2012

(30) Foreign Application Priority Data

Jan. 31, 2011 (JP) ................. 2011-018032

(51) Int. Cl.
 *C09K 19/20* (2006.01)
 *C07C 255/56* (2006.01)
 *G02F 1/133* (2006.01)
 *C09K 19/54* (2006.01)

(52) U.S. Cl.
 USPC ............ 428/1.1; 252/299.67; 252/299.5; 558/416

(58) Field of Classification Search
 USPC ............ 560/65; 570/127, 130; 558/416; 252/299.67, 299.65; 428/1.1; 349/182
 See application file for complete search history.

(56) References Cited

U.S. PATENT DOCUMENTS

| 5,733,477 | A | 3/1998 | Kondo et al. |
| 6,051,288 | A | 4/2000 | Kondo et al. |

(Continued)

FOREIGN PATENT DOCUMENTS

| JP | 2006-348226 | 12/2006 |
| JP | 2007-308534 | 11/2007 |

(Continued)

OTHER PUBLICATIONS

Yokokoji et al., "Synthesis of new Chiral Compounds for Cholesteric Liquid Crystal Display", Liquid Crystals, Aug. 1, 2008, vol. 35, No. 8, pp. 995-1003.

(Continued)

*Primary Examiner* — Shean C Wu
(74) *Attorney, Agent, or Firm* — Nixon Peabody LLP; Jeffrey L. Costellia

(57) ABSTRACT

A novel liquid crystalline compound and/or a liquid crystal composition including the novel liquid crystalline compound that can be used for a variety of liquid crystal devices capable of exhibiting a blue phase with a wide temperature range are/is provided. A liquid crystalline compound represented by the general formula (G1) is provided. In the general formula (G1), n is an integer of 2 to 10

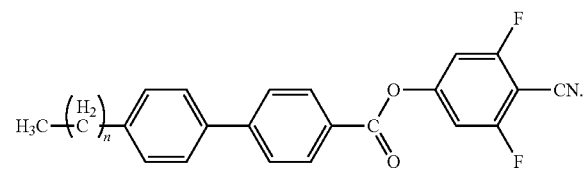

(G1)

13 Claims, 12 Drawing Sheets

(56) References Cited

U.S. PATENT DOCUMENTS

| | | | |
|---|---|---|---|
| 6,551,670 B2 * | 4/2003 | Tahara et al. | 428/1.3 |
| 7,576,829 B2 | 8/2009 | Kikuchi et al. | |
| 7,648,647 B2 | 1/2010 | Kikuchi et al. | |
| 8,440,102 B2 * | 5/2013 | Tamura et al. | 252/299.66 |
| 2008/0259254 A1 | 10/2008 | Kikuchi et al. | |
| 2011/0284797 A1 * | 11/2011 | Tamura et al. | 252/299.66 |

FOREIGN PATENT DOCUMENTS

| | | |
|---|---|---|
| JP | 2008-303381 | 12/2008 |
| WO | WO 96-32365 | 10/1996 |
| WO | WO 2005-080529 | 9/2005 |
| WO | WO-2005/080529 A1 | 9/2005 |
| WO | WO 2005-090520 A1 | 9/2005 |
| WO | WO 2011/145536 A1 | 11/2011 |

OTHER PUBLICATIONS

International Search Report (Application No. PCT/JP2012/051483; PCT14625) Dated Apr. 24, 2012.
Written Opinion (Application No. PCT/JP2012/051463; PCT14625) Dated Apr. 24, 2012.
Office Action (Application No. 13/104,202; US13549/14626) Dated Oct. 5, 2012.
International Search Report (Application No. PCT/JP2011/061117; PCT13549/14626) Dated Aug. 2, 2011.
Written Opinion (Application No. PCT/JP2011/061117; PCT13549/14626) Dated Aug. 2, 2011.
Office Action (U.S. Appl. No. 13/104,202; US13549/14626) Dated Oct. 5, 2012.

* cited by examiner

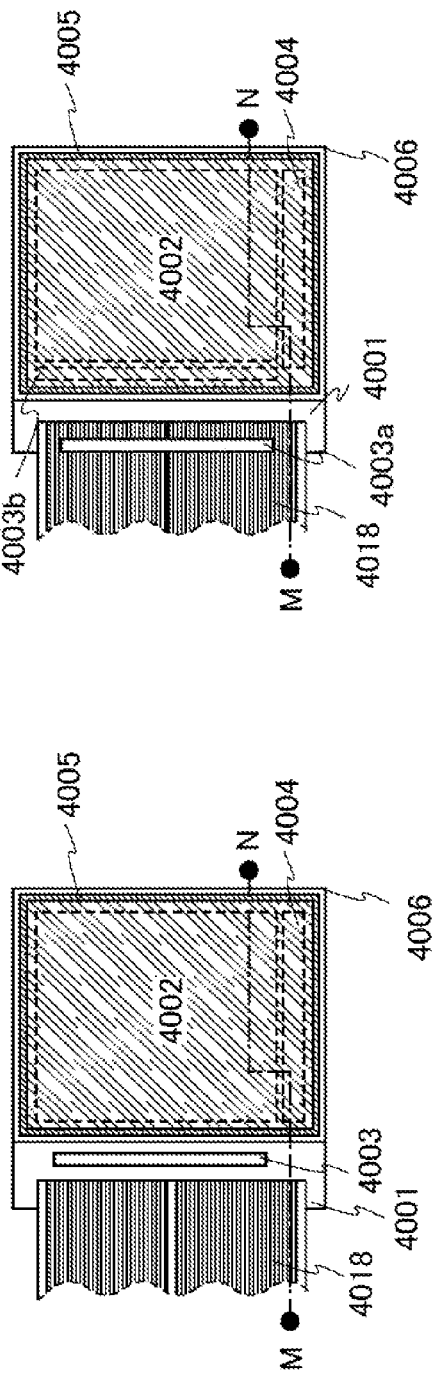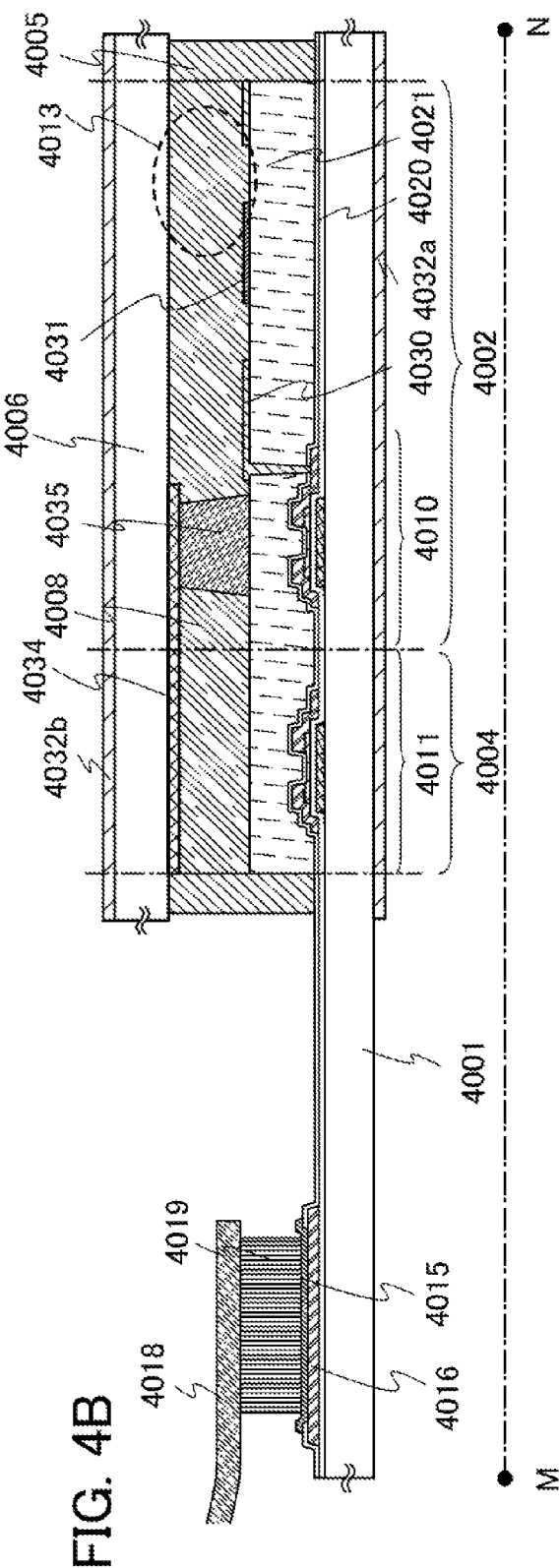
FIG. 4A1
FIG. 4A2
FIG. 4B

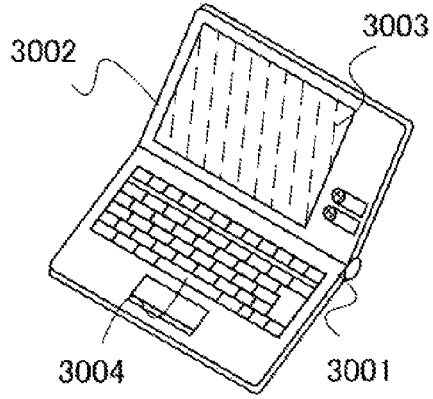
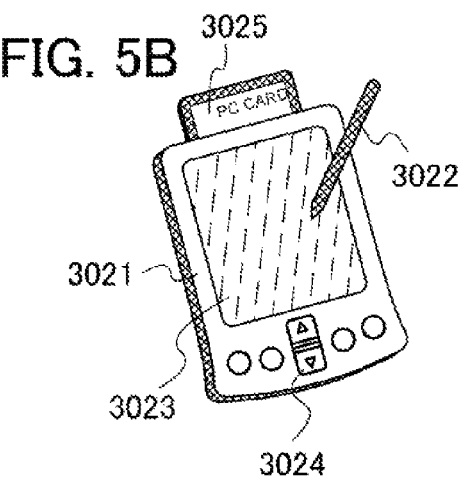
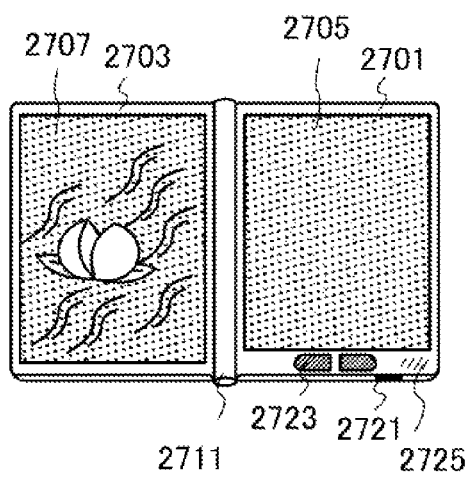
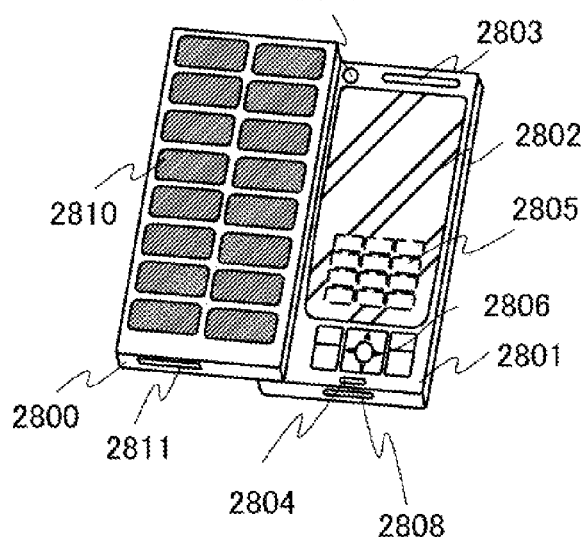
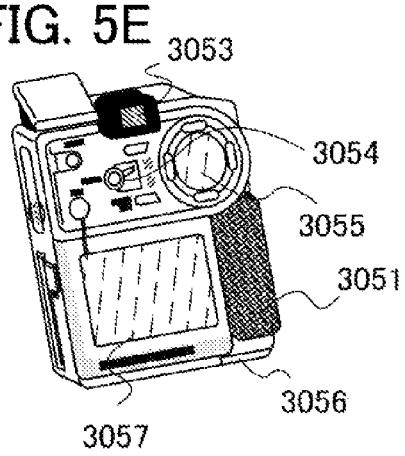
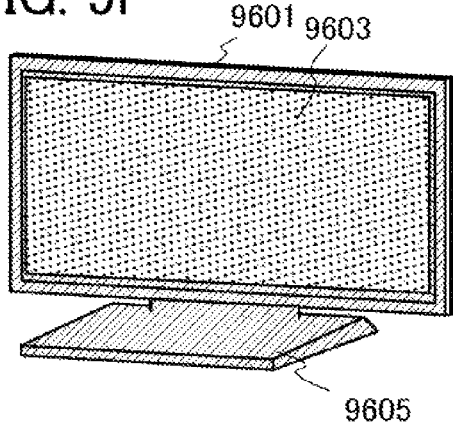

LIQUID CRYSTALLINE COMPOUND, LIQUID CRYSTAL COMPOSITION, LIQUID CRYSTAL ELEMENT, AND LIQUID CRYSTAL DISPLAY DEVICE

TECHNICAL FIELD

The present invention relates to a liquid crystalline compound, a liquid crystal composition, a liquid crystal element, and a liquid crystal display device, and manufacturing methods thereof.

BACKGROUND ART

In recent years, liquid crystal has been applied to a variety of devices; in particular, a liquid crystal display device (liquid crystal display) having advantages of thinness and lightness has been used for displays in a wide range of fields.

For a larger and higher-resolution display screen, higher response speed of liquid crystal has been demanded, and development thereof has been advanced (for example, see Patent Document 1).

As a display mode of liquid crystal capable of high-speed response, a display mode using liquid crystal exhibiting a blue phase is given. The mode using liquid crystal exhibiting a blue phase achieves high-speed response, does not require an alignment film, and provides a wide viewing angle, and thus has been developed more actively for practical use (for example, see Patent Document 2).

REFERENCE

Patent Document

[Patent Document 1] Japanese Published Patent Application No. 2008-303381
[Patent Document 2] PCT International Publication No. 2005-090520

DISCLOSURE OF INVENTION

An object is to provide a novel liquid crystalline compound that can be used for a variety of liquid crystal devices.

In particular, an object is, with the use of the novel liquid crystalline compound, to provide a liquid crystal composition with a wide temperature range where a blue phase is exhibited.

Another object is to achieve high contrast of a liquid crystal element and a liquid crystal display device with the use of the liquid crystalline compound or the liquid crystal composition.

According to one embodiment of the present invention, a liquid crystalline compound represented by the general formula (G1), (4-(4-n-alkylphenyl)benzoic acid 4-cyano-3,5-difluorophenyl (abbreviation: PPEP-nFCNF)), is provided.

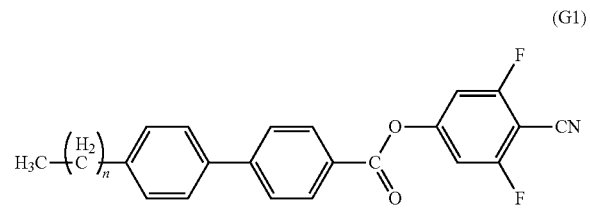

(G1)

In the general formula (G1), n is an integer of 2 to 10.

According to another embodiment of the present invention, a liquid crystal composition including the liquid crystalline compound (PPEP-nFCNF (n is an integer of 2 to 10) (abbreviation)) is provided.

According to another embodiment of the present invention, a liquid crystal composition including the liquid crystalline compound (PPEP-nFCNF (n is an integer of 2 to 10) (abbreviation)), and another liquid crystalline compound and/or a chiral agent is provided.

According to one embodiment of the present invention, the above liquid crystal composition is a liquid crystal composition capable of exhibiting a blue phase.

According to another embodiment of the present invention, a liquid crystal element or a liquid crystal device in which the above liquid crystalline compound or the above liquid crystal composition is used is provided.

A novel liquid crystalline compound (PPEP-nFCNF (n is an integer of 2 to 10) (abbreviation)) can be provided. A liquid crystal composition including the liquid crystalline compound (PPEP-nFCNF (n is an integer of 2 to 10) (abbreviation)) and having a wide temperature range where a blue phase is exhibited can be provided.

A liquid crystal element or a liquid crystal display device which includes the liquid crystalline compound (PPEP-nFCNF (n is an integer of 2 to 10) (abbreviation)) or a liquid crystal composition and achieves higher contrast can be provided. Therefore, a liquid crystal display device having high visibility and high image quality can be provided.

BRIEF DESCRIPTION OF DRAWINGS

FIGS. 4A1, 4A2, and 4B illustrate liquid crystal display modules.

FIGS. 5A to 5F illustrate electronic devices.

BEST MODE FOR CARRYING OUT THE INVENTION

Figure 1A:
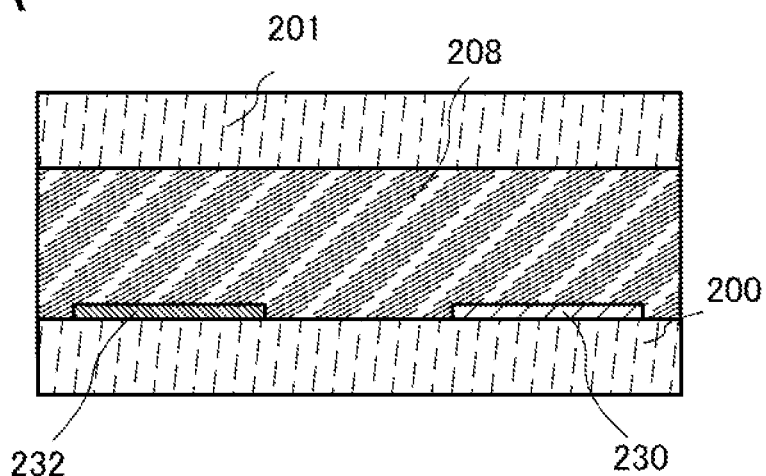
FIGS. 1A and 1B are conceptual views each illustrating a liquid crystal element or a liquid crystal display device including a liquid crystalline compound and a liquid crystal composition.

Embodiments and Examples of the present invention will be described in detail with reference to the accompanying drawings. Note that the present invention is not limited to the following description, and it will be easily understood by those skilled in the art that various changes and modifications can be made without departing from the spirit and scope of the present invention. Therefore, the present invention should not be construed as being, limited to the description in the following embodiments. In the structures described below, the same portions or portions having similar functions are denoted by the same reference numerals in different drawings, and explanation thereof will not be repeated.

Note that the ordinal numbers such as "first", "second", and "third" in this specification are used for convenience and do not denote the order of steps and the stacking order of layers. In addition, the ordinal numbers in this specification do not denote particular names which specify the present invention.

Embodiment 1

Figure 1B:
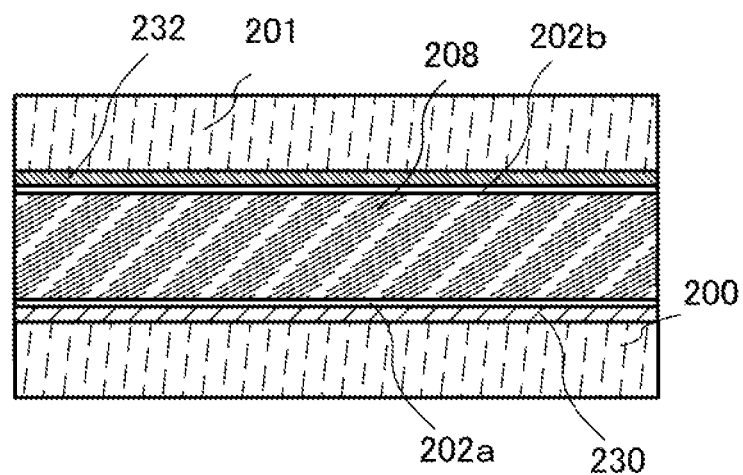

A liquid crystalline compound, a liquid crystal composition, and a liquid crystal element or a liquid crystal display device including the liquid crystalline compound or the liquid crystal composition according to one embodiment of the present invention will be described with reference to FIGS. 1A and 1B. FIGS. 1A and 1B are each a cross-sectional view of a liquid crystal element or a liquid crystal display device.

A liquid crystalline compound according to one embodiment of the present invention is a liquid crystalline compound (PPEP-nFCNF (n is an integer of 2 to 10) (abbreviation)) represented by the general formula (G1).

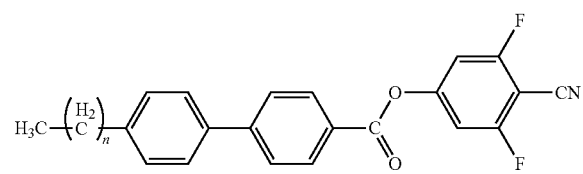

(G1)

In the general formula (G1), n is an integer of 2 to 10.

Specific examples of the liquid crystalline compound (PPEP-nFCNF (n is an integer of 2 to 10) (abbreviation)) include 4-(4-n-propylphenyl)benzoic acid 4-cyano-3,5-difluorophenyl (abbreviation: PPEP-3FCNF) represented by the structural formula (103), 4-(4-n-butylphenyl)benzoic acid 4-cyano-3,5-difluorophenyl (abbreviation: PPEP-4FCNF) represented by the structural formula (104), 4-(4-n-pentylphenyl)benzoic acid 4-cyano-3,5-difluorophenyl (abbreviation: PPEP-5FCNF) represented by the structural formula (105), 4-(4-n-hexylphenyl)benzoic acid 4-cyano-3,5-difluorophenyl (abbreviation: PPEP-6FCNF) represented by the structural formula (106), 4-(4-n-heptylphenyl)benzoic acid 4-cyano-3,5-difluorophenyl (abbreviation: PPEP-7FCNF) represented by the structural formula (107), 4-(4-n-octylphenyl)benzoic acid 4-cyano-3,5-di Fluorophenyl (abbreviation: PPEP-8FCNF) represented by the structural formula (108), 4-(4-n-nonylphenyl)benzoic acid 4-cyano-3,5-difluorophenyl (abbreviation: PPEP-9FCNF) represented by the structural formula (109), 4-(4-n-decylphenyl)benzoic acid 4-cyano-3,5-difluorophenyl (abbreviation: PPEP-10FCNF) represented by the structural formula (110), and 4-(4-n-dodecylphenyl)benzoic acid 4-cyano-3,5-d fluorophenyl (abbreviation: PPEP-11FCNF) represented by the structural formula (111).

(103)

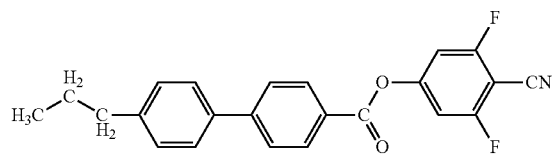

PPEP-3FCNF (104)

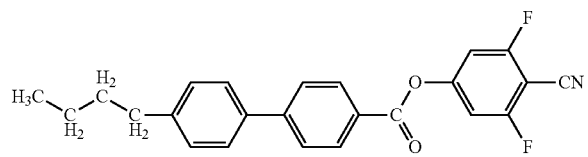

PPEP-4FCNF (105)

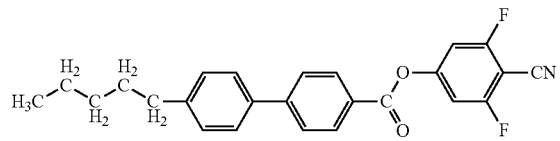

PPEP-5FCNF (106)

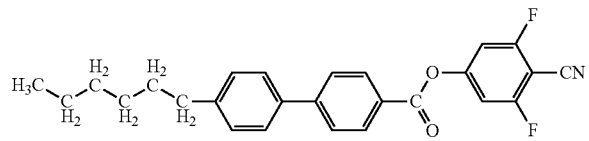

PPEP-6FCNF (107)

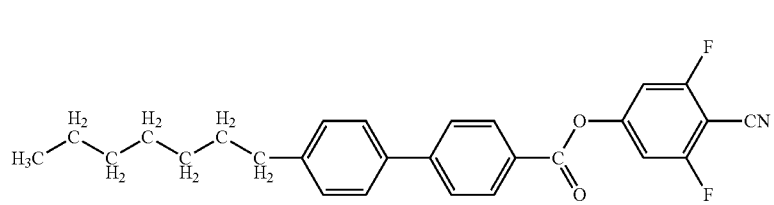

PPEP-7FCNF (108)

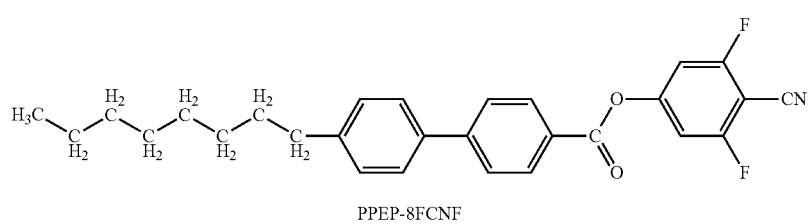

PPEP-8FCNF

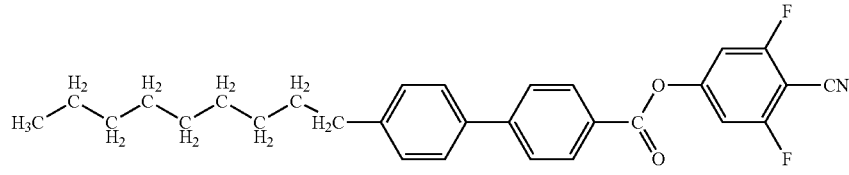

PPEP-9FCNF (109)

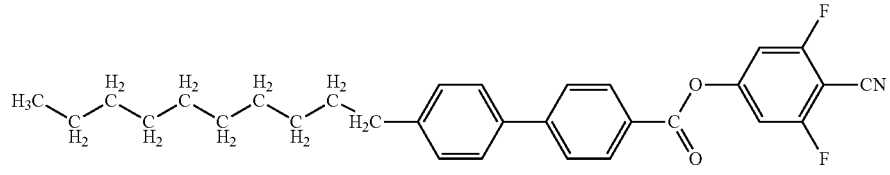

PPEP-10FCNF (110)

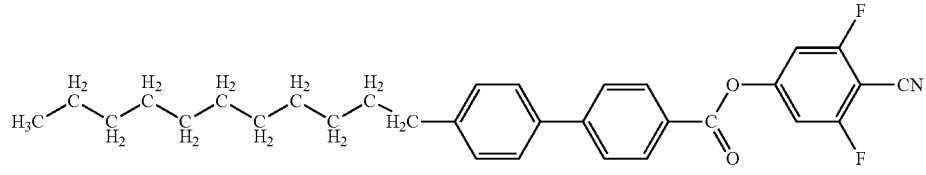

PPEP-11FCNF (111)

A variety of reactions can be applied to a synthesis method of the liquid crystalline compound (PPEP-nFCNF (n is an integer of 2 to 10) (abbreviation)) according to one embodiment of the present invention. For example, through a synthesis reaction shown in the following synthetic scheme (A-1), the liquid crystalline compound (PPEP-nFCNF (n is an integer of 2 to 10) (abbreviation)) represented by the general formula (G1) according to one embodiment of the present invention can be synthesized. Note that a synthesis method of the liquid crystalline compound (PPEP-nFCNF (n is an integer of 2 to 10) (abbreviation)) according to one embodiment of the present invention is not limited to the following synthesis method.

A synthesis method of a compound illustrated in the following general formula (G1) will be described.

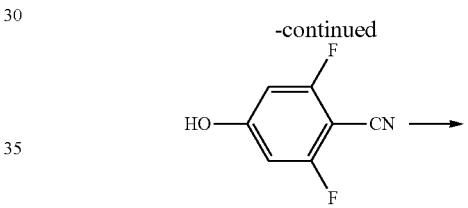

(G1)

In the above general formula (G1), n represents an integer of 2 to 10. First, a synthesis method of the compound illustrated in the general formula (G1) will be described referring to the following reaction formula (G-1).

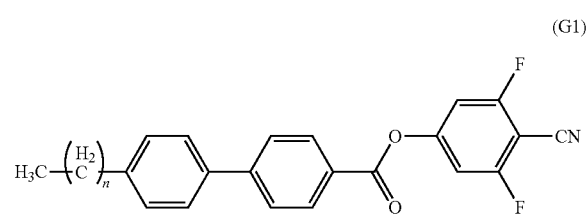

(G-1)

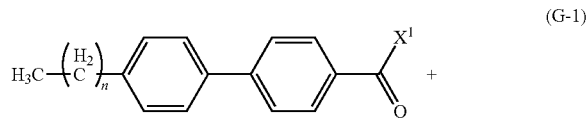

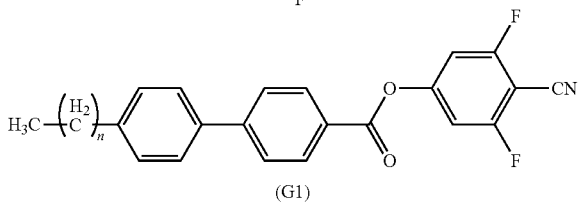

(G1)

The esterification reaction of 4-(n-alkylphenyl)benzoic acid (Compound 1) and 4-hydroxy-2,6-difluorobenzonitrile (Compound 2) can give a target substance, 4-(4-n-alkylphenyl)benzoic acid 4-cyano-3,5-difluorophenyl (G1) (reaction formula (G-1)). In the reaction formula (G-1), n represents an integer of 2 to 10, and X1 represents chlorine or a hydroxyl group.

In the case where X1 is a hydroxyl group, as the esterification reaction, an esterification reaction in which dehydration condensation using an acid catalyst is performed (addition-elimination reaction) is given. In the case where a dehydration condensation reaction is performed, an acid catalyst such as concentrated sulfuric acid or para-toluenesulfonic acid, 1-ethyl-3-(3-dimethylaminopropyl)carbodiimide hydrochloride (abbreviation: EDC), dicyclohexyl carbodiimide (abbreviation: DCC), or the like can be used. In the case where EDC or DCC is used, EDC is preferable because a by-product can be easily removed. The synthesis of the target substance (G1) is not limited to such reactions.

Next, a synthesis method of the compound illustrated in the general formula (G1) will be described referring to the following reaction formula (G-2).

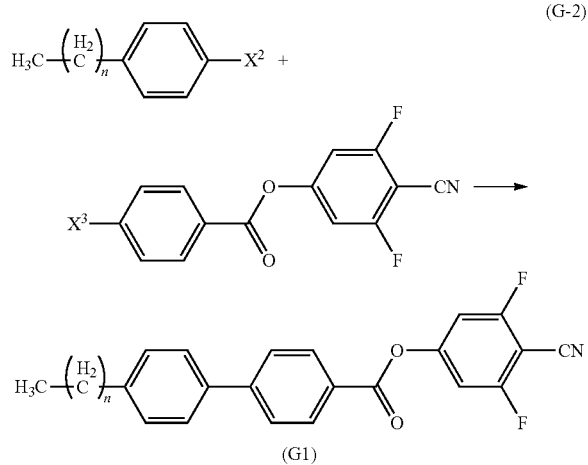

(G-2)

(G1)

The coupling reaction of an n-alkylphenyl compound (Compound 3) and a benzoic acid 4-cyano-2,6-difluorophenyl compound (Compound 4) can give a target substance, 4-(4-n-alkylphenyl)benzoic acid 4-cyano-3,5-difluorophenyl (G1) (reaction formula (G-2)). In the reaction formula (G-2), n represents an integer of 2 to 10, X2 represents boronic acid, an organoboron group, a halogenated zinc group, an organotin group, a halogenated magnesium group, or the like, and X3 represents chlorine, bromine, iodine, a trifluoromethanesulfonate group, or the like.

As the above reaction, Suzuki-Miyaura coupling, Negishi coupling, Kumada-Tamao-Corriu coupling, Migita-Kosugi-Stille coupling, and the like are given. As a catalyst that can be used in the case where such reactions occur, tetrakis(triphenylphosphine)palladium(0), palladium(II) chloride, bis(triphenylphosphine)palladium(II)dichloride, palladium(II) acetate, [1,2-bis(diphenylphosphino)ethane]nickel(II) dichloride, and the like are given. In such reactions, water and alcohol are not preferably used in order to suppress generation of a by-product. The synthesis of the target substance (G1) is not limited to such reactions.

In the above manner, the liquid crystalline compound (PPEP-nFCNF (n is an integer of 2 to 10) (abbreviation)) according to one embodiment of the present invention can be synthesized.

A liquid crystal composition according to one embodiment of the present invention includes the liquid crystalline compound (PPEP-nFCNF (n is an integer of 2 to 10) (abbreviation)).

A liquid crystal element and a liquid crystal display device according to one embodiment of the present invention include the liquid crystalline compound (PPEP-nFCNF (abbreviation)) or a liquid crystal composition including the liquid crystalline compound (PPEP-nFCNF (abbreviation)).

A liquid crystal composition according to one embodiment of the present invention includes the liquid crystalline compound, (PPEP-nFCNF (n is an integer of 2 to 10) (abbreviation)). In addition, the liquid crystal composition further includes another liquid crystalline compound, a non-liquid-crystalline compound, and/or a chiral agent. A liquid crystal composition including at least the liquid crystalline compound (PPEP-nFCNF (n is an integer of 2 to 10) (abbreviation)) and a chiral agent can be used as a liquid crystal composition exhibiting a blue phase.

A liquid crystal composition including the liquid crystalline compound (PPEP-nFCNF (n is an integer of 2 to 10) (abbreviation)) and a chiral agent has a wide temperature range where a blue phase is exhibited. Therefore, the liquid crystal composition is not easily changed in characteristics and is stable even when being used for a variety of applications accompanied by temperature change. Thus, the liquid crystal composition has high reliability.

A liquid crystal composition according to one embodiment of the present invention includes the liquid crystalline compound (PPEP-nFCNF (11 is an integer of 2 to 10) (abbreviation)), and one or more kinds of liquid crystalline compounds (PPEP-nFCNF (n is an integer of 2 to 10) (abbreviation)) may be used. The liquid crystal composition may include another liquid crystalline compound or a non-liquid-crystalline compound; for example, 4-(4-n-methylphenyl)benzoic acid 4-cyano-3,5-difluorophenyl (abbreviation: PPEP-1FCNF) represented by the structural formula (101), 4-(4-ethylphenyl)benzoic acid 4-cyano-3,5-difluorophenyl (abbreviation: PPEP-2FCNF) represented by the structural formula (102), 4-(trans-4-n-propylcyclohexyl)-3',4'-difluoro-1,1'-biphenyl (abbreviation: CPP-3FF), 4-n-pentylbenzoic acid 4-cyano-3-fluorophenyl (abbreviation: PEP-5CNF), or the like can be used.

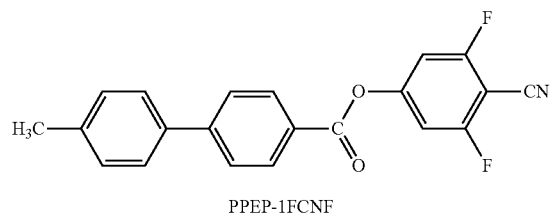

PPEP-1FCNF (101)

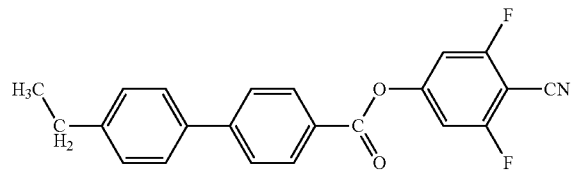

PPEP-2FCNF (102)

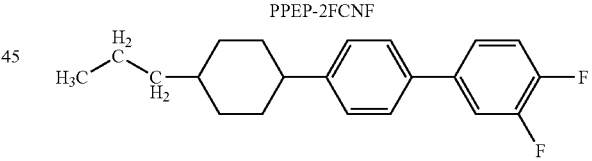

CPP-3FF

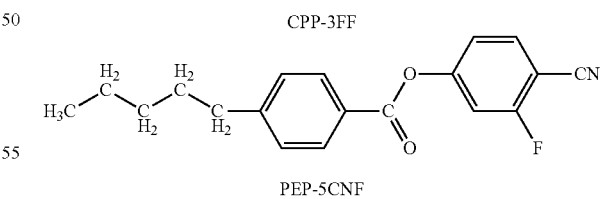

PEP-5CNF

The chiral agent is used to induce twisting of the liquid crystal composition, align the liquid crystal composition in a helical structure; and make the liquid crystal composition exhibit a blue phase. For the chiral agent, a compound which has an asymmetric center, high compatibility with the liquid crystal composition, and strong twisting power is used. In addition, the chiral agent is an optically active substance; a higher optical purity is better and the most preferable optical purity is 99% or higher.

A blue phase is optically isotropic and thus has no viewing angle dependence. Consequently, an alignment film is not necessarily formed; therefore, display image quality can be improved and cost can be reduced.

In a liquid crystal display device, it is preferable that a polymerizable monomer be added to a liquid crystal composition and polymer stabilization treatment be performed in order to broaden the temperature range where a blue phase is exhibited. As the polymerizable monomer, for example, a thermopolymerizable (thermosetting) monomer which can be polymerized by heat, a photopolymerizable (photocurable) monomer which can be polymerized by light, or a polymerizable monomer which can be polymerized by heat and light can be used. Further, a polymerization initiator may be added to the liquid crystal composition.

The polymerizable monomer may be a monofunctional monomer such as acrylate or methacrylate; a polyfunctional monomer such as diacrylate, triacrylate, dimethacrylate, or trimethacrylate; or a mixture thereof. Further, the polymerizable monomer may have liquid crystallinity, non-liquid crystallinity, or both of them.

As the polymerization initiator, a radical polymerization initiator which generates radicals by light irradiation, an acid generator which generates an acid by light irradiation, or a base generator which generates a base by light irradiation may be used.

For example, polymer stabilization treatment can be performed in such a manner that a photopolymerizable monomer and a photopolymerization initiator are added to the liquid crystal composition and the liquid crystal composition is irradiated with light having a wavelength at which the photopolymerizable monomer and the photopolymerization initiator react. As the photopolymerizable monomer, typically, a UV polymerizable monomer can be used. When a UV polymerizable monomer is used as a photopolymerizable monomer, the liquid crystal composition may be irradiated with ultraviolet light.

This polymer stabilization treatment may be performed on a liquid crystal composition exhibiting an isotropic phase or a liquid crystal composition exhibiting a blue phase under the control of the temperature. A temperature at which the phase changes from a blue phase to an isotropic phase when the temperature rises, or a temperature at which the phase changes from an isotropic phase to a blue phase when the temperature falls is referred to as the phase transition temperature between a blue phase and an isotropic phase. For example, the polymer stabilization treatment can be performed in the following manner: after a liquid crystal composition to which a photopolymerizable monomer is added is heated to exhibit an isotropic phase, the temperature of the liquid crystal composition is gradually lowered so that the phase changes to a blue phase, and then, light irradiation is performed while the temperature at which a blue phase is exhibited is kept.

FIGS. 1A and 1B illustrate examples of a liquid crystal element and a liquid crystal display device according to one embodiment of the present invention.

A liquid crystal element according to one embodiment of the present invention includes at least, between a pair of electrode layers (a pixel electrode layer 230 and a common electrode layer 232 having different potentials), the liquid crystalline compound (PPEP-nFCNF (n is an integer of 2 to 10) (abbreviation)) or a liquid crystal composition 208 including the liquid crystalline compound (PPEP-nFCNF (n is an integer of 2 to 10) (abbreviation)).

FIGS. 1A and 1B each illustrate a liquid crystal element and a liquid crystal display device in which a first substrate 200 and a second substrate 201 are positioned so as to face each other with a liquid crystal composition 208 which includes a liquid crystal composition exhibiting a blue phase interposed between the first substrate 200 and the second substrate 201. A difference between the liquid crystal element and the liquid crystal display device in FIG. 1A and those in FIG. 1B is positions of the pixel electrode layer 230 and the common electrode layer 232 relative to the liquid crystal composition 208.

In the liquid crystal element and the liquid crystal display device illustrated in FIG. 1A, the pixel electrode layer 230 and the common electrode layer 232 are provided between the first substrate 200 and the liquid crystal composition 208 so as to be adjacent to each other. With the structure in FIG. 1A, a method in which the gray scale is controlled by generating an electric field substantially parallel (i.e., in a lateral direction) to a substrate to move liquid crystal molecules in a plane parallel to the substrate can be used.

The structure in FIG. 1A can be favorably applied to the case where the liquid crystal composition 208 is formed using a liquid crystal composition including the liquid crystalline compound exhibiting a blue phase, which is a liquid crystal composition according to one embodiment of the present invention. The liquid crystal composition provided as the liquid crystal composition 208 may contain an organic resin.

With an electric field generated between the pixel electrode layer 230 and the common electrode layer 232, liquid crystal is controlled. An electric field in a lateral direction is generated for the liquid crystal, so that liquid crystal molecules can be controlled using the electric field. The liquid crystal composition exhibiting a blue phase is capable of high-speed response. Thus, a high-performance liquid crystal element and a high-performance liquid crystal display device can be achieved. That is, the liquid crystal molecules aligned to exhibit a blue phase can be controlled in a direction parallel to the substrate, whereby a wide viewing angle is obtained.

For example, such a liquid crystal composition exhibiting a blue phase, which is capable of high-speed response, can be favorably used for a successive additive color mixing method (field sequential method) in which light-emitting diodes (LEDs) of RGB or the like are arranged in a backlight unit and color display is performed by time division, or a three-dimensional display method using a shutter glasses system in which images for the right eye and images for the left eye are alternately viewed by time division.

In the liquid crystal element and the liquid crystal display device illustrated in FIG. 1B, the pixel electrode layer 230 and the common electrode layer 232 are provided on the first substrate 200 side and the second substrate 201 side respectively, with the liquid crystal composition 208 interposed therebetween. With the structure in FIG. 1B, a method in which the gray scale is controlled by generating an electric field substantially perpendicular to a substrate to move liquid crystal molecules in a plane perpendicular to the substrate can be used. An alignment film 202a and an alignment film 202b may be provided between the liquid crystal composition 208 and the pixel electrode layer 230 and between the liquid crystal composition 208 and the common electrode layer 232, respectively. A liquid crystal composition according to one embodiment of the present invention can be used in liquid crystal elements with a variety of structures and liquid crystal display devices with a variety of display modes.

The distance between the pixel electrode layer 230 and the common electrode layer 232, which are adjacent to each other with the liquid crystal composition 208 interposed therebetween, is a distance at which liquid crystal in the liquid crystal composition 208 between the pixel electrode layer 230 and the common electrode layer 232 responds to a predetermined voltage applied between the pixel electrode layer 230 and the common electrode layer 232. The voltage applied is controlled depending on the distance as appropriate.

The maximum thickness (film thickness) of the liquid crystal composition 208 is preferably greater than or equal to 1 μm and less than or equal to 20 μm.

The liquid crystal composition 208 can be formed by a dispenser method (dropping method), or an injection method in which liquid crystal is injected using capillary action or the like after the first substrate 200 and the second substrate 201 are attached to each other.

Although not illustrated in FIGS. 1A and 1B, an optical film such as a polarizing plate, a retardation plate, or an anti-reflection film, or the like is provided as appropriate. For example, circular polarization with the polarizing plate and the retardation plate may be used. In addition, a backlight or the like can be used as a light source.

In this specification, a substrate provided with a semiconductor element (e.g., a transistor), a pixel electrode layer, and a common electrode layer is referred to as an element substrate (a first substrate), and a substrate which faces the element substrate with a liquid crystal composition interposed therebetween is referred to as a counter substrate (a second substrate).

As a liquid crystal display device according to one embodiment of the present invention, a transmissive liquid crystal display device in which display is performed by transmission of light from a light source, a reflective liquid crystal display device in which display is performed by reflection of incident light, or a transflective liquid crystal display device in which a transmissive type and a reflective type are combined can be provided.

In the case of the transmissive liquid crystal display device, a pixel electrode layer, a common electrode layer, a first substrate, a second substrate, and other components such as an insulating film and a conductive film, which are provided in a pixel region through which light is transmitted, have a property of transmitting light in the visible wavelength range. In the liquid crystal display device having the structure illustrated in FIG. 1A, it is preferable that the pixel electrode layer and the common electrode layer have a light-transmitting property; however, if an opening pattern is provided, a non-light-transmitting material such as a metal film may be used depending on the shape.

On the other hand, in the case of the reflective liquid crystal display device, a reflective component which reflects light transmitted through the liquid crystal composition (e.g., a reflective film or substrate) may be provided on the side opposite to the viewing side of the liquid crystal composition. Therefore, a substrate, an insulating film, and a conductive film which are provided between the viewing side and the reflective component and through which light is transmitted have a light-transmitting property with respect to light in the visible wavelength range. Note that in this specification, a light-transmitting property refers to a property of transmitting at least light in the visible wavelength range. In the liquid crystal display device having the structure illustrated in FIG. 1B, the pixel electrode layer or the common electrode layer on the side opposite to the viewing side may have a light-reflecting property so that it can be used as a reflective component.

The pixel electrode layer 230 and the common electrode layer 232 may be formed using, one or more of the following: indium tin oxide (ITO), a conductive material in which zinc oxide (ZnO) is mixed into indium oxide (indium zinc oxide), a conductive material in which silicon oxide ($SiO_2$) is mixed into indium oxide, organoindium, organotin, indium oxide containing tungsten oxide, indium zinc oxide containing tungsten oxide, indium oxide containing titanium oxide, and indium tin oxide containing titanium oxide; graphene; metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

As the first substrate 200 and the second substrate 201, a glass substrate of barium borosilicate glass, aluminoborosilicate glass, or the like, a quartz substrate, a plastic substrate, or the like can be used.

Therefore, a novel liquid crystalline compound (PPEP-nFCNF (n is an integer of 2 to 10) (abbreviation)) can be provided. A liquid crystal composition including the liquid crystalline compound (PPEP-nFCNF (n is an integer of 2 to 10) (abbreviation)) and having a wide temperature range where a blue phase is exhibited can be provided.

With the use of the liquid crystalline compound (PPEP-nFCNF (n is an integer of 2 to 10) (abbreviation)) or a liquid crystal composition including the liquid crystalline compound (PPEP-nFCNF (n is an integer of 2 to 10) (abbreviation)), a liquid crystal element or a liquid crystal display device which achieves higher contrast can be provided. Thus, a liquid crystal display device with high visibility and high image quality can be provided.

This embodiment can be implemented in appropriate combination with any of the structures described in the other embodiments.

Embodiment 2

As a liquid crystal display device according to one embodiment of the present invention, a passive matrix liquid crystal display device and an active matrix liquid crystal display device can be provided. In this embodiment, an example of an active matrix liquid crystal display device according to one embodiment of the present invention will be described with reference to FIGS. 2A and 2B and FIGS. 3A to 3D.

Figure 2A:
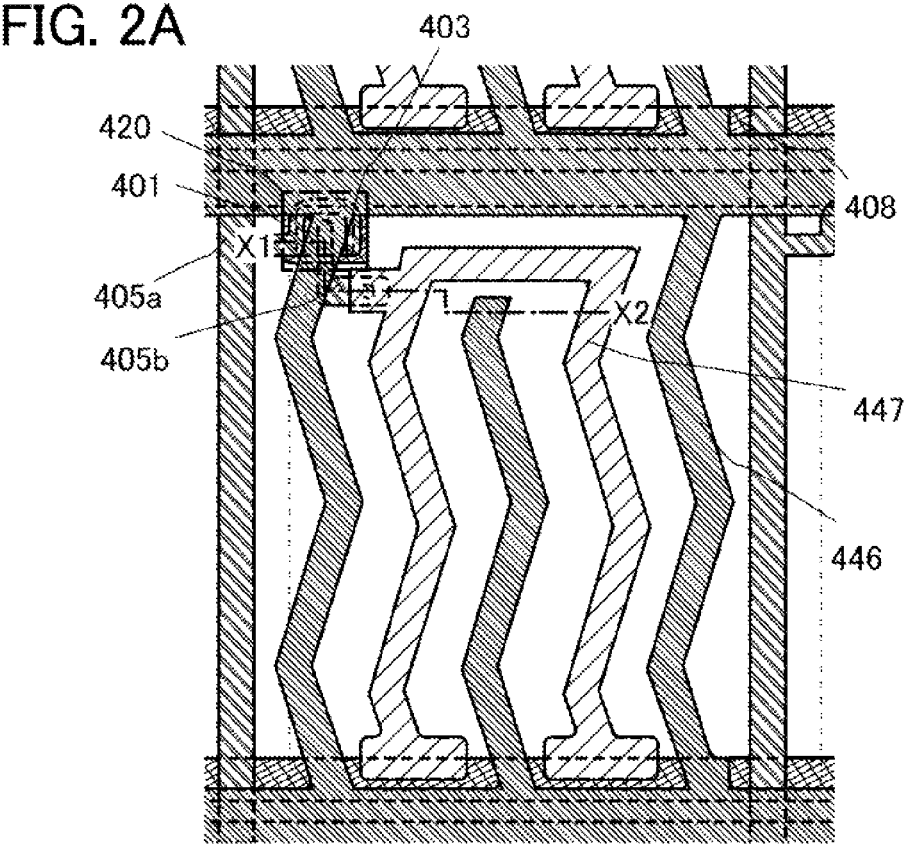
FIGS. 2A and 2B illustrate one mode of a liquid crystal display device.
Figure 2B:
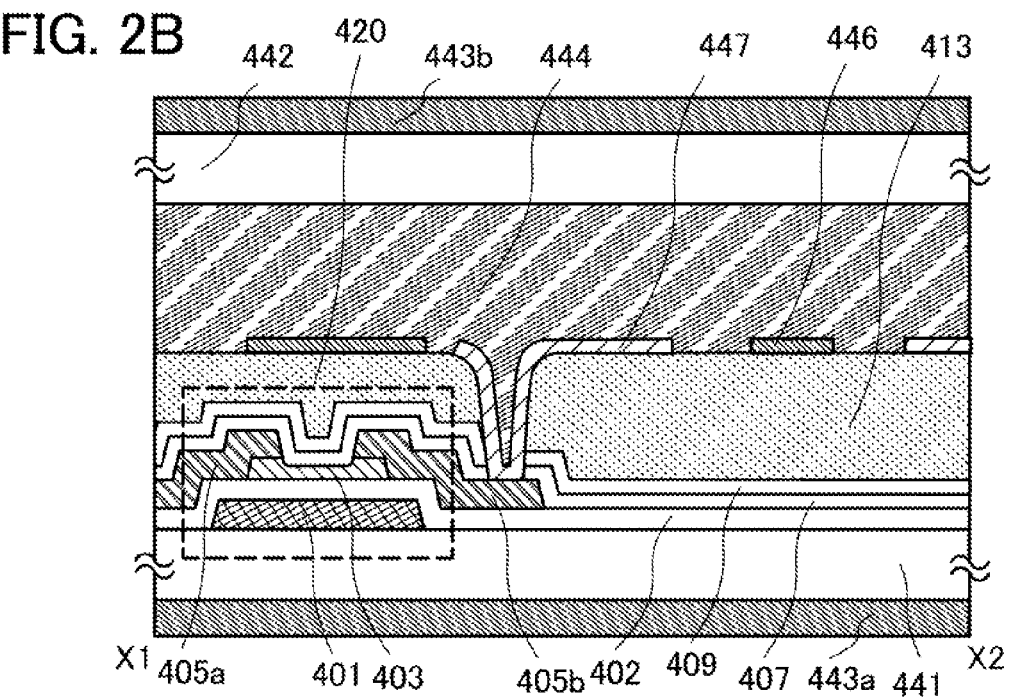

FIG. 2A is a plan view of the liquid crystal display device and illustrates one pixel. FIG. 2B is a cross-sectional view taken along line X1-X2 in FIG. 2A.

In FIG. 2A, a plurality of source wiring layers (including a wiring layer 405a) is arranged so as to be parallel to (extend in the longitudinal direction in the drawing) and apart from each other. A plurality of gate wiring layers (including a gate electrode layer 401) is arranged so as to be extended in a direction perpendicular to or substantially perpendicular to the source wiring layers (in the horizontal direction in the drawing) and apart from each other. Common wiring layers 408 are provided so as to be adjacent to the corresponding gate wiring layers and extended in a direction parallel to or substantially parallel to the gate wiring layers, that is, in a direction perpendicular to or substantially perpendicular to the source wiring layers (in the horizontal direction in the drawing). A roughly rectangular space is surrounded by the source wiring layers, the common wiring layer 408, and the gate wiring layer. In this space, a pixel electrode layer and a common electrode layer of the liquid crystal display device are provided. A transistor 420 for driving the pixel electrode layer is provided at the upper left corner of the drawing. A plurality of pixel electrode layers and a plurality of transistors are arranged in matrix.

In the liquid crystal display device in FIGS. 2A and 2B, a first electrode layer 447 electrically connected to the transistor 420 serves as a pixel electrode layer, while a second electrode layer 446 electrically connected to the common wiring layer 408 serves as a common electrode layer. Note that a capacitor is formed by the first electrode layer and the common siring layer. Although the common electrode layer can operate in a floating state (electrically isolated state), the potential of the common electrode layer may be set to a fixed potential, preferably to a potential around a common potential (intermediate potential of an image signal which is transmitted as data) at such a level as not to generate flickers.

A method can be used in which the gray scale is controlled by generating an electric field parallel to or substantially parallel to a substrate (i.e., in the lateral direction) to move liquid crystal molecules in a plane parallel to the substrate. For such a method, an electrode structure used in an IPS mode illustrated in FIGS. 2A and 2B and FIGS. 3A to 3D can be employed.

In a lateral electric field mode such as an IPS mode, a first electrode layer (e.g., a pixel electrode layer with which a voltage is controlled in each pixel) and a second electrode layer (e.g., a common electrode layer with which a common voltage is applied to all pixels), each of which has an opening pattern, are located below a liquid crystal composition. Therefore, the first electrode layer 447 and the second electrode layer 446, one of which is a pixel electrode layer and the other of which is a common electrode layer, are formed over a first substrate 441, and at least one of the first electrode layer and the second electrode layer is formed over an interlayer film. The first electrode layer 447 and the second electrode layer 446 have not a flat shape but various opening patterns including a bent portion or a branched comb-like portion. The first electrode layer 447 and the second electrode layer 446 do not have the same shape or do not overlap with each other in order to generate an electric field between the electrodes.

The first electrode layer 447 and the second electrode layer 446 may have an electrode structure used in an FFS mode. In a lateral electric field mode such as an FFS mode, a first electrode layer (e.g., a pixel electrode layer with which a voltage is controlled in each pixel) having an opening pattern is located below a liquid crystal composition, and further, a second electrode layer (e.g., a common electrode layer with which a common voltage is applied to all pixels) having a flat shape is located below the opening pattern. In this case, the first electrode layer and the second electrode layer, one of which is a pixel electrode layer and the other of which is a common electrode layer, are formed over the first substrate 441, and the pixel electrode layer and the common electrode layer are stacked with an insulating film (or an interlayer insulating film) interposed therebetween. One of the pixel electrode layer and the common electrode layer is formed below the other and has a flat shape, whereas the other is formed above the one and has various opening patterns including a bent portion or a branched comb-like portion. The first electrode layer 447 and the second electrode layer 446 do not have the same shape or do not overlap with each other in order to generate an electric field between the electrodes.

The liquid crystalline compound (PPEP-nFCNF (n is an integer of 2 to 10) (abbreviation)) described in Embodiment 1 or a liquid crystal composition including the liquid crystalline compound (PPEP-nFCNF (n is an integer of 2 to 10) (abbreviation)) is used for a liquid crystal composition 444. The liquid crystal composition 444 may further contain an organic resin. In this embodiment, the liquid crystal composition 444 including the liquid crystalline compound (PPEP-nFCNF (n is an integer of 2 to 10) (abbreviation)) is subjected to polymer stabilization treatment, which is provided in the liquid crystal display device with a blue phase exhibited (with a blue phase shown).

With an electric field generated between the first electrode layer 447 as the pixel electrode layer and the second electrode layer 446 as the common electrode layer, liquid crystal of the liquid crystal composition 444 is controlled. An electric field in the lateral direction is formed for the liquid crystal, so that liquid crystal molecules can be controlled using the electric field. Since the liquid crystal molecules aligned to exhibit a blue phase can be controlled in the direction parallel to the substrate, a wide viewing angle is obtained.

Figure 3A:
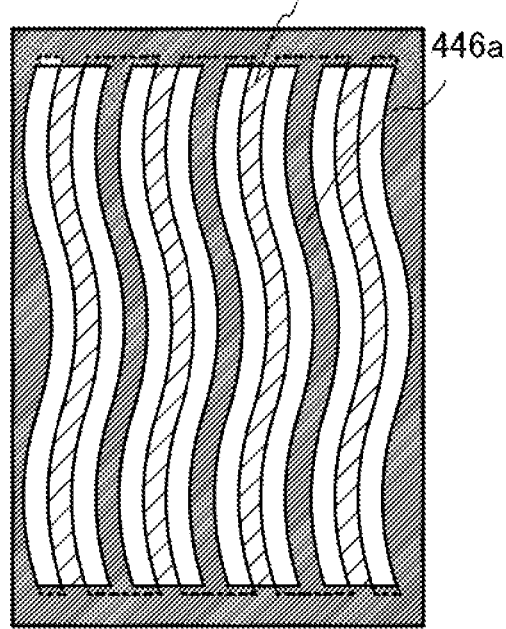
FIGS. 3A to 3D each illustrate one mode of an electrode structure of a liquid crystal display device.
Figure 3B:
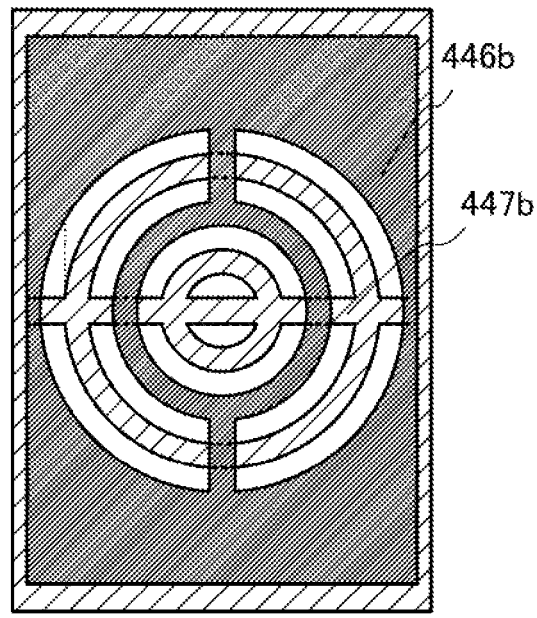
Figure 3C:
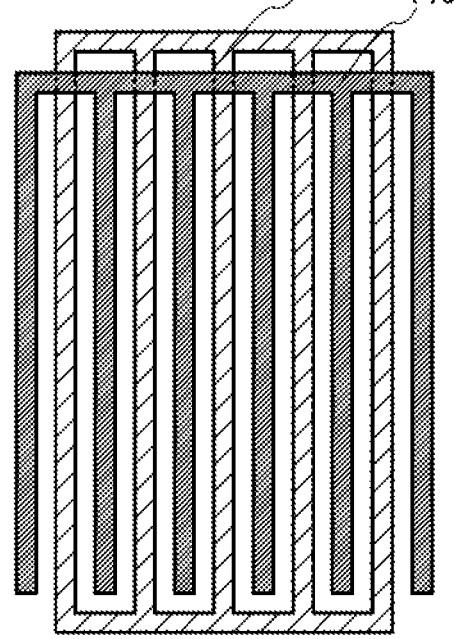
Figure 3D:
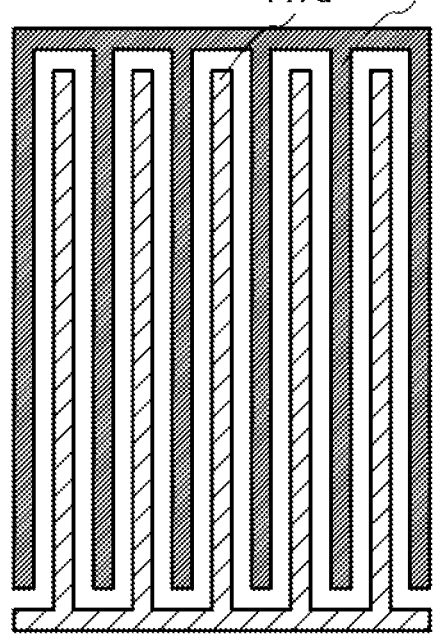

FIGS. 3A to 3D illustrate other examples of the first electrode layer 447 and the second electrode layer 446. As illustrated in top views of FIGS. 3A to 3D, first electrode layers 447*a* to 447*d* and second electrode layers 446*a* to 446*d* are arranged alternately. In FIG. 3A, the first electrode layer 447*a* and the second electrode layer 446*a* have wavelike shapes with curves. In FIG. 3B, the first electrode layer 447*b* and the second electrode layer 446*b* have shapes with concentric circular openings. In FIG. 3C, the first electrode layer 447*c* and the second electrode layer 446*c* have comb-like shapes and partially overlap with each other. In FIG. 3D, the first electrode layer 447*d* and the second electrode layer 446*d* have comb-like shapes in which the electrode layers are engaged with each other. In the case where the first electrode layers 447*a*, 447*b*, and 447*c* overlap with the second electrode layers 446*a*, 446*b*, and 446*c*, respectively, as illustrated in FIGS. 3A to 3C, an insulating film is formed between the first electrode layer 447 and the second electrode layer 446 so that the first electrode layer 447 and the second electrode layer 446 are formed over different films.

Since the first electrode layer 447 and the second electrode layer 446 have opening patterns, they are illustrated as divided plural electrode layers in the cross-sectional view in FIG. 2B. The same applies to the other drawings of this specification.

The transistor 420 is an inverted staggered thin film transistor in which the gate electrode layer 401, a gate insulating layer 402, a semiconductor layer 403, and wiring layers 405*a* and 405*b* which function as a source electrode layer and a drain electrode layer are formed over the first substrate 441 having an insulating surface.

There is no particular limitation on the structure of a transistor which can be used for a liquid crystal display device disclosed in this specification. For example, a staggered type or a planar type having a top-gate structure or a bottom-gate structure can be employed. The transistor may have a single-gate structure in which one channel formation region is formed, a double-gate structure in which two channel formation regions are formed, or a triple-gate structure in which three channel formation regions are formed. Alternatively, the transistor may have a dual-gate structure including two gate electrode layers positioned over and below a channel region with a gate insulating layer interposed therebetween.

An insulating film 407 which is in contact with the semiconductor layer 403, and an insulating film 409 are provided to cover the transistor 420. An interlayer film 413 is stacked over the insulating film 409.

There is no particular limitation on the method for forming the interlayer film 413, and the following method can be employed depending on the material: spin coating, dip coating, spray coating, a droplet discharging method (such as an ink-jet method), a printing method (such as screen printing or offset printing), roll coating, curtain coating, knife coating, or the like.

The first substrate 441 and a second substrate 442 which is a counter substrate are firmly attached to each other with a sealant with the liquid crystal composition 444 interposed therebetween. The liquid crystal composition 444 can be formed by a dispenser method (a dropping method), or an injection method in which liquid crystal is injected using capillary action or the like after the first substrate 441 is attached to the second substrate 442.

As the sealant, typically, a visible light curable resin, a UV curable resin, or a thermosetting resin, is, preferably used. Typically, an acrylic resin, an epoxy resin, an amine resin, or the like can be used. Further, a photopolymerization initiator (typically, a UV polymerization initiator), a thermosetting agent, a filler, or a coupling agent may be contained in the sealant.

In order to perform polymer stabilization treatment on the liquid crystal composition 444 by light irradiation, used in this embodiment is a liquid crystal composition which includes the liquid crystalline compound (PPEP-nFCNF (n is an integer of 2 to 10) (abbreviation)) described in Embodiment 1, a chiral agent, and a liquid crystal composition exhibiting a blue phase and to which a photopolymerizable monomer and a photopolymerization are added.

After the space between the first substrate 441 and the second substrate 442 is filled with the liquid crystal composition, polymer stabilization treatment is performed by light irradiation, whereby the liquid crystal composition 444 is formed. The light has a wavelength with which the photopolymerizable monomer and the photopolymerization initiator which are contained in the liquid crystal composition used as the liquid crystal composition 444 react. By such polymer stabilization treatment by light irradiation, the temperature range where the liquid crystal composition 444 exhibits a blue phase can be broadened.

A liquid crystal composition which includes the liquid crystalline compound (PPEP-nFCNF (n is an integer of 2 to 10) (abbreviation)) and a chiral agent and exhibits a blue phase has a wider temperature range where a blue phase is exhibited. Therefore, the liquid crystal composition is not easily changed in characteristics and is stable even when being used for a variety of applications accompanied by temperature change. Thus, a liquid crystal element and a liquid crystal display device including the liquid crystal composition can have high reliability.

In the case where a photocurable resin such as a UV curable resin is used as a sealant and a liquid crystal composition is formed by a dropping method, for example, the sealant may be cured in the light irradiation step of the polymer stabilization treatment.

In this embodiment, a polarizing plate 443a is provided on the outer side (on the side opposite to the liquid crystal composition 444) of the first substrate 441, and a polarizing plate 443b is provided on the outer side (on the side opposite to the liquid crystal composition 444) of the second substrate 442. In addition to the polarizing plate, an optical film such as a retardation plate or an anti-reflection film may be provided. For example, circular polarization with the polarizing plate and the retardation plate may be used. Through the above process, a liquid crystal display device can be completed.

In the case of manufacturing a plurality of liquid crystal display devices using a large-sized substrate (a so-called multiple panel method), a division step can be performed before performing the polymer stabilization treatment or before providing the polarizing plates in consideration of the influence of the division step on the liquid crystal composition (such as alignment disorder due to force applied in the division step), it is preferable: that the division step be performed after attaching the first substrate and the second substrate and before performing the polymer stabilization treatment.

Although not illustrated, a backlight, a sidelight, or the like may be used as a light source. Light from the light source is emitted from the side of the first substrate 441 which is an element substrate so as to pass through the second substrate 442 on the viewing side.

The first electrode layer 447 and the second electrode layer 446 can be formed using a light-transmitting conductive material such as indium oxide containing tungsten oxide, indium zinc oxide containing tungsten oxide, indium oxide containing titanium oxide, indium tin oxide containing titanium oxide, indium tin oxide (hereinafter referred to as ITO), indium zinc oxide, indium tin oxide to which silicon oxide is added, or graphene.

The first electrode layer 447 and the second electrode layer 446 can be formed of one or more materials selected from metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu) and silver (Ag); alloys thereof; and metal nitrides thereof.

The first electrode layer 447 and the second electrode layer 446 can be formed using a conductive composition including a conductive macromolecule (also referred to as a conductive polymer). The pixel electrode formed using the conductive composition preferably has a sheet resistance of 10000 $\Omega$/square or less and a transmittance of 70% or more at a wavelength of 550 nm. Further, the resistivity of the conductive macromolecule included in the conductive composition is preferably less than or equal to 0.1 $\Omega$·cm.

As the conductive macromolecule, a so-called $\pi$-electron conjugated conductive macromolecule can be used. For example, polyaniline or a derivative thereof, polypyrrole or a derivative thereof, polythiophene or a derivative thereof, a copolymer of two or more kinds of aniline, pyrrole, and thiophene or a derivative thereof, and the like can be given.

An insulating film serving as a base film may be provided between the first substrate 441 and the gate electrode layer 401. The base film has a function of preventing diffusion of an impurity element from the first substrate 441, and can be formed to have a single-layer structure or a layered structure using one or more of a silicon nitride film, a silicon oxide film, a silicon nitride oxide film, and a silicon oxynitride film. The gate electrode layer 401 can be formed to have a single-layer structure or a layered structure using any of metal materials such as molybdenum, titanium, chromium, tantalum, tungsten, aluminum, copper, neodymium, and scandium, and an alloy material which contains any of these materials as its main component. By using a light-blocking conductive film as the gate electrode layer 401, light from a backlight (light emitted through the first substrate 441) can be prevented from entering the semiconductor layer 403.

For example, as a two-layer structure of the gate electrode layer 401, the following structures are preferable: a two-layer structure of an aluminum layer and a molybdenum layer stacked thereover, a two-layer structure of a copper layer and a molybdenum layer stacked thereover, a two-layer structure, of a copper layer and a titanium nitride layer or a tantalum nitride layer stacked thereover, and a two-layer structure of a titanium nitride layer and a molybdenum layer. As a three-layer structure, a layered structure in which a tungsten layer or a tungsten nitride layer, an alloy layer of aluminum and silicon or an alloy layer of aluminum and titanium, and a titanium nitride layer or a titanium layer are stacked is preferable.

The gate insulating layer 402 can be formed to have a single-layer structure or a layered structure using any of a silicon oxide layer, a silicon nitride layer, a silicon oxynitride layer, and a silicon nitride oxide layer by a plasma CVD method, a sputtering method, or the like. Alternatively, the gate insulating layer 402 can be formed using a silicon oxide layer by a CVD method using an organosilane gas. As an organosilane gas, a silicon-containing compound such as tetraethoxysilane (TEOS) (chemical formula: $Si(OC_2H_5)_4$), tetramethylsilane (TMS) (chemical formula: $Si(CH_3)_4$), tetramethylcyclotetrasiloxane (TMCTS), octamethylcyclotetrasiloxane, (OMCTS), hexamethyldisilazane (HMDS), triethoxysilane ($SiH(OC_2H_5)_3$), or trisdimethylaminosilane ($SiH(N(CH_3)_2)_3$) can be used.

A material of the semiconductor layer 403 is not particularly limited and may be determined as appropriate depending on characteristics needed for the transistor 420. Examples of a material which can be used for the semiconductor layer 403 will be described.

The semiconductor layer 403 can be formed using the following material: an amorphous semiconductor manufactured by a sputtering method or a vapor-phase growth method using a semiconductor source gas typified by silane or germane; a polycrystalline semiconductor formed by crystallizing the amorphous semiconductor with the use of light energy or thermal energy; a microcrystalline semiconductor; or the like. The semiconductor layer can be formed by a sputtering method, an LPCVD method, a plasma CVD method, or the like.

A typical example of an amorphous semiconductor is hydrogenated amorphous silicon, while a typical example of a crystalline semiconductor is polysilicon. Examples of polysilicon (polycrystalline silicon) are as follows: so-called high-temperature polysilicon which contains polysilicon formed at a process temperature of 800° C. or higher as its main component, so-called low-temperature polysilicon which contains polysilicon formed at a process temperature of 600° C. or lower as its main component, and polysilicon obtained by crystallizing amorphous silicon with the use of an element that promotes crystallization, or the like. It is needless to say that a microcrystalline semiconductor or a semiconductor partly containing a crystal phase can be used as described above.

Further, an oxide semiconductor may be used. As the oxide semiconductor, an oxide of four metal elements such as an In—Sn—Ga—Zn—O-based oxide semiconductor; an oxide of three metal elements such as an In—Ga—Zn—O-based oxide semiconductor, an In—Sn—Zn—O-based oxide semiconductor, an In—Al—Zn—O-based oxide semiconductor, a Sn—Ga—Zn—O-based oxide semiconductor, an Al—Ga—Zn—O-based oxide semiconductor, or a Sn—Al—Zn—O-based oxide semiconductor; or an oxide of two metal elements such as an In—Zn—O-based oxide semiconductor, a Sn—Zn—O-based oxide semiconductor, an Al—Zn—O-based oxide semiconductor, a Zn—Mg—O-based oxide semiconductor, a Sn—Mg—O-based oxide semiconductor, an In—Mg—O-based oxide semiconductor, or an In—Ga—O-based oxide semiconductor; an In—O-based oxide semiconductor; a Sn—O-based oxide semiconductor; or a Zn—O-based oxide semiconductor can be used. Further, $SiO_2$ may be contained in the above oxide semiconductor. Here, for example, an In—Ga—Zn—O-based oxide semiconductor is an oxide containing at least In, Ga, and Zn, and there is no particular limitation on the composition ratio thereof. Further, the In—Ga—Zn—O-based oxide semiconductor may contain an element other than In, Ga, and Zn.

For the oxide semiconductor layer, a thin film expressed by the chemical formula, $InMO_3(ZnO)_m$ (m>0), can be used. Here, M represents one or more metal elements selected from Ga, Al, Mn, and Co. For example, M can be Ga, Ga and Al, Ga and Mn, or Ga and Co.

In the case where an In—Zn—O-based material is used as the oxide semiconductor, the atomic ratio is set so that In/Zn is in a range from 0.5 to 50, preferably from 1 to 20, more preferably from 1.5 to 15. When the atomic ratio of Zn is in the above-described range, a transistor can be improved in field-effect mobility. Here, when the atomic ratio of the compound is In:Zn:O=X:Y:Z, the relation Z>1.5X+Y is satisfied.

The oxide semiconductor layer can be formed using an oxide including a crystal with c-axis alignment (also referred to as a c-axis aligned crystal (CAAC)), which has neither a single crystal structure nor an amorphous structure.

In a process of forming the semiconductor layer and the wiring layer, an etching step is used to process thin films into desired shapes. Dry etching or wet etching can be employed for the etching step.

The etching conditions (such as an etchant, etching time, and temperature) are appropriately adjusted depending on the material so that the material can be etched to have a desired shape.

As a material of the wiring layers 405a and 405b serving as source and drain electrode layers, an element selected from Al, Cr, Ta, Ti, Mo, and W; an alloy containing any of the above elements as its component; an alloy film containing a combination of any of these elements; and the like can be given. Further, in the case where heat treatment is performed, the conductive film preferably has heat resistance against the heat treatment. Since the use of aluminum alone brings disadvantages such as low heat resistance and a tendency to corrosion, aluminum is used in combination with a conductive material having heat resistance. As the conductive material having heat resistance, which is combined with aluminum, it is possible to use an element selected from titanium (Ti), tantalum (Ta), tungsten (W), molybdenum (Mo), chromium (Cr), neodymium (Nd), and scandium (Sc); an alloy containing any of these elements as its component; an alloy containing a combination of any of these elements; or a nitride containing any of these elements as its component.

The gate insulating layer 402, the semiconductor layer 403, and the wiring layers 405a and 405b serving as source and drain electrode layers may be successively formed without being exposed to the air. Successive film formation without exposure to the air makes it possible to obtain each interface between stacked layers, which is not contaminated by atmospheric components or impurity elements floating in the air. Therefore, variation in characteristics of the transistor can be reduced.

Note that the semiconductor layer 403 is partly etched so as to have a groove (a depressed portion).

As the insulating film 407 and the insulating film 409 which cover the transistor 420, an inorganic insulating film or an organic insulating film formed by a dry method or a wet method can be used. For example, it is possible to use a silicon nitride film, a silicon oxide film, a silicon oxynitride film, an aluminum oxide film, or a tantalum oxide film, which is formed by a CVD method, a sputtering method, or the like. Alternatively, an organic material such as polyimide, acrylic, benzocyclobutene, polyamide, or epoxy can be used. As an alternative to such organic materials, it is possible to use a low-dielectric constant material (a low-k material), a siloxane-based resin, phosphosilicate glass (PSG), borophosphosilicate glass (BPSG), or the like. A gallium oxide film can also be used as the insulating film 407.

Note that the siloxane-based resin corresponds to a resin including a Si—O—Si bond formed using a siloxane-based material as a starting material. The siloxane-based resin may include as a substituent an organic group (e.g., an alkyl group or an aryl group) or a fluoro group. The organic group may include a fluoro group. A siloxane-based resin is applied by a coating method and baked; thus, the insulating film 407 can be formed.

Alternatively, the insulating film 407 and the insulating film 409 may be formed by stacking a plurality of insulating films formed using any of these materials. For example, a structure may be employed in which an organic resin film is stacked over an inorganic insulating film.

Further, with the use of a resist mask having regions with plural thicknesses (typically, two different thicknesses) which is formed using a multi-tone mask, the number of resist masks can be reduced, resulting in a simplified process and lower cost.

As described above, with the use of the liquid crystalline compound (PPEP-nFCNF (n is an integer of 2 to 10) (abbreviation)) or the liquid crystal composition, a liquid crystal element or a liquid crystal display device which achieves higher contrast can be provided. Thus, a liquid crystal display device with high visibility and high image quality can be provided.

Since a liquid crystal composition including the liquid crystalline compound (PPEP-nFCNF (n is an integer of 2 to 10) (abbreviation)) and exhibiting a blue phase is capable of high-speed response, a high-performance liquid crystal display device can be achieved.

This embodiment can be implemented in appropriate combination with any of the structures described in the other embodiments.

Embodiment 3

A liquid crystal display device having a display function can be manufactured by manufacturing transistors and using the transistors for a pixel portion and further for a driver circuit. Further, part or the whole of the driver circuit can be formed over the same substrate as the pixel portion, using the transistor, whereby a system-on-panel can be obtained.

The liquid crystal display device includes a liquid crystal element (also referred to as a liquid crystal display element) as a display element.

Further, a liquid crystal display device includes a panel in which a liquid crystal display element is sealed, and a module in which an IC or the like including a controller is mounted to the panel. One embodiment of the present invention also relates to an element substrate, which corresponds to one mode in which the display element has not been completed in a manufacturing process of the liquid crystal display device, and the element substrate is provided with a means for supplying current to the display element in each of a plurality of pixels. Specifically, the element substrate may be in a state where it is provided only with a pixel electrode of the display element, in a state where a conductive film to be a pixel electrode has been formed and the conductive film has not yet been etched to form the pixel electrode, or in any other state.

Note that a liquid crystal display device in this specification means an image display device, a display device, or a light-source (including a lighting device). Further, the liquid crystal display device includes any of the following modules in its category: a module to which a connector such as a flexible printed circuit (FPC), tape automated bonding (TAB) tape, or a tape carrier package (TCP) is attached; a module having TAB tape or a TCP which is provided with a printed wiring board at the end thereof; and a module having an integrated circuit (IC) directly mounted on a display element by a chip on glass (COG) method.

The appearance and a cross section of a liquid crystal display panel, which is one embodiment of a liquid crystal display device, will be described with reference to FIGS. 4A1, 4A2, and 4B. FIGS. 4A1 and 4A2 are each a top view of a panel in which transistors 4010 and 4011 formed over a first substrate 4001 and a liquid crystal element 4013 are sealed between the first substrate 4001 and a second substrate 4006 with a sealant 4005. FIG. 4B is a cross-sectional view taken along line M-N of FIGS. 4A1 and 4A2.

The sealant 4005 is provided to surround a pixel portion 4002 and a scanning line driver circuit 4004 that are provided over the first substrate 4001. The second substrate 4006 is provided over the pixel portion 4002 and the scanning line driver circuit 4004. Therefore, the pixel portion 4092 and the scanning line driver circuit 4004 are sealed together with a liquid crystal composition 4008, by the first substrate 4001, the sealant 4005, and the second substrate 4006.

In FIG. 4A1, a signal line driver circuit 4003 that is formed using a single crystal semiconductor film or a polycrystalline semiconductor film over a substrate separately prepared is mounted in a region different from the region surrounded by the sealant 4005 over the first substrate 4001. Note that FIG. 4A2 illustrates an example in which part of the signal line driver circuit is formed using a transistor provided over the first substrate 4001. A signal line driver circuit 4003b is formed over the first substrate 4001, and a signal line driver circuit 4003a formed using a single crystal semiconductor film or a polycrystalline semiconductor film is mounted on a substrate separately prepared.

Note that there is no particular limitation on the connection method of a driver circuit which is separately formed, and COG, wire bonding, TAB, or the like can be used. FIG. 4A1 illustrates an example of mounting the signal line driver circuit 4003 by COG, and FIG. 4A2 illustrates an example of mounting the signal line driver circuit 4003a by TAB.

The pixel portion 4002 and the scanning line driver circuit 4004 provided over the first substrate 4001 each include a plurality of transistors. FIG. 4B illustrates the transistor 4010 included in the pixel portion 4002 and the transistor 4011 included in the scanning line driver circuit 4004. An insulating layer 4020 and an interlayer film 4021 are provided over the transistors 4010 and 4011.

As the transistors 4010 and 4011, the transistor which is described in Embodiment 2 or 3 can be employed.

Further, a conductive layer may be provided over the interlayer film 4021 or the insulating layer 4020 so as to overlap with a channel formation region of a semiconductor layer of the transistor 4011 for the driver circuit. The conductive layer may have the same potential as or a potential different from that of a gate electrode layer of the transistor 4011 and can function as a second gate electrode layer. Further, the potential of the conductive layer may be GND or 0 V, or the conductive layer may be in a floating state.

A pixel electrode layer 4030 and a common electrode layer 4031 are provided over the interlayer film 4021, and the pixel electrode layer 4030 is electrically connected to the transistor 4010. The liquid crystal element 4013 includes the pixel electrode layer 4030, the common electrode layer 4031, and the liquid crystal composition 4008. Note that a polarizing plate 4032a and a polarizing plate 4032b are provided on the outer sides of the first substrate 4001 and the second substrate 4006, respectively.

The liquid crystalline compound (PPEP-nFCNF (n is an integer of 2 to 10) (abbreviation)) described in Embodiment 1 or a liquid crystal composition including the liquid crystalline compound (PPEP-nFCNF (n is an integer of 2 to 10) (abbreviation)) is used for the liquid crystal composition 4008. The structures of the pixel electrode layer and the common electrode layer described in Embodiment 1 or 2 can be used for the pixel electrode layer 4030 and the common electrode layer 4031.

In this embodiment, the liquid crystal composition 4008 including the liquid crystalline compound (PPEP-nFCNF (n is an integer of 2 to 10) (abbreviation)) and the chiral agent is subjected to polymer stabilization treatment, which is provided in the liquid crystal display device with a blue phase exhibited (with a blue phase shown). Therefore, in this embodiment, the pixel electrode layer 4030 and the common electrode layer 4031 have opening patterns illustrated in FIG. 1A described in Embodiment 1 or FIGS. 3A to 3D described in Embodiment 2.

With an electric field generated between the pixel electrode layer 4030 and the common electrode layer 4031, liquid crystal of the liquid crystal composition 4008 is controlled. An electric field in a lateral direction is formed for the liquid crystal, so that liquid crystal molecules can be controlled using the electric field. Since the liquid crystal molecules aligned to exhibit a blue phase can be controlled in a direction parallel to the substrate, a wide viewing angle is obtained.

A liquid crystal composition which includes the liquid crystalline compound (PPEP-nFCNF (n is an integer of 2 to 10) (abbreviation)) and a chiral agent and exhibits a blue phase has a wider temperature range where a blue phase is exhibited. Therefore, the liquid crystal composition is not easily changed in characteristics and is stable even when being used for a variety of applications accompanied by temperature change. Thus, a liquid crystal element and a liquid crystal display device including the liquid crystal composition can have high reliability.

As the first substrate 4001 and the second substrate 4006, glass, plastic, or the like having a light-transmitting property can be used. As plastic, a fiberglass-reinforced plastics (FRP) plate, a polyvinyl fluoride (PVF) film, a polyester film, or an acrylic resin film can be used. A sheet with a structure in which an aluminum foil is sandwiched between PVF films or polyester films can also be used.

A columnar spacer denoted by reference numeral 4035 is obtained by selective etching of an insulating film and is provided in order to control the thickness of the liquid crystal composition 4008 (a cell gap). Alternatively, a spherical spacer may be used. In the liquid crystal display device including the liquid crystal composition 4008, the cell gap which is the thickness of the liquid crystal composition is preferably greater than or equal to 1 µm and less than or equal to 20 µm. In this specification, the thickness of a cell gap refers to the maximum thickness (film thickness) of a liquid crystal composition.

Although FIGS. 4A1, 4A2, and 4B illustrate examples of transmissive liquid crystal display devices, one embodiment of the present invention can also be applied to a transflective liquid crystal display device and a reflective liquid crystal display device.

FIGS. 4A1, 4A2, and 4B illustrate examples of liquid crystal display devices in which a polarizing plate is provided on the outer side (the viewing side) of a substrate; however, the polarizing plate may be provided on the inner side of the substrate. The position of the polarizing plate may be determined as appropriate depending on the material of the polarizing plate and conditions of the manufacturing process. Furthermore, a light-blocking layer serving as a black matrix may be provided.

A color filter layer or a light-blocking layer may be formed as part of the interlayer film 4021. In FIGS. 4A1, 4A2, and 4B a light-blocking layer 4034 is provided on the second substrate 4006 side so as to cover the transistors 4010 and 4011. By providing the light-blocking layer 4034, the contrast can be more increased and the transistors can be more stabilized.

The transistors may be, but is not necessarily, covered with the insulating layer 4020 which functions as a protective film of the transistors.

Note that the protective film is provided to prevent entry of contaminant impurities such as an organic, substance, metal, and moisture floating in the air and, is preferably a dense film. The protective film may be formed by a sputtering method to have a single-layer structure or a layered structure including any of a silicon oxide film, a silicon nitride film, a silicon, oxynitride film, a silicon nitride oxide film, an aluminum oxide film, an aluminum nitride film, an aluminum oxynitride film, and an aluminum nitride oxide film.

Further, in the case of further forming a light-transmitting insulating layer as a planarizing insulating film, the light-transmitting insulating layer can be formed using an organic material having heat resistance, such as polyimide, acrylic, benzocyclobutene, polyamide, or epoxy. As an alternative to such organic materials, it is possible to use a low-dielectric constant material (a low-k material), a siloxane-based resin, phosphosilicate glass (PSG), borophosphosilicate glass (BPSG), or the like. The insulating layer may be formed by stacking a plurality of insulating films formed of these materials.

There is no particular limitation on the method for forming the insulating layer having a stacked structure, and the following method can be employed depending on the material: sputtering, spin coating, dip coating, spray coating, a droplet discharging method (such as an ink-jet method), a printing method (such as screen printing or offset printing), roll coating, curtain coating, knife coating, or the like.

The pixel electrode layer 4030 and the common electrode layer 4031 can be formed using a light-transmitting conductive material such as indium oxide containing tungsten oxide, indium zinc oxide containing tungsten oxide, indium oxide containing titanium oxide, indium tin oxide containing titanium oxide, indium tin oxide (hereinafter referred to as ITO), indium zinc oxide, indium tin oxide to which silicon oxide is added, or graphene.

Alternatively, the pixel electrode layer 4030 and the common electrode layer 4031 can be formed using one or more of the following: metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and nitrides thereof.

The pixel electrode layer 4030 and the common electrode layer 4031 can be formed using a conductive composition including a conductive macromolecule (also referred to as a conductive polymer).

Further, a variety of signals and potentials are supplied to the signal line driver circuit 4003 which is formed separately, the scanning line driver circuit 4004, or the pixel portion 4002 from an FPC 4018.

Further, since the transistor is easily broken by static electricity or the like, a protective circuit for protecting the driver circuits is preferably provided over the same substrate as a gate line or a source line. The protection circuit is preferably formed using a nonlinear element.

In FIGS. 4A1, 4A2, and 4B, a connection terminal electrode 4015 is formed using the same conductive film as the pixel electrode layer 4030, and a terminal electrode 4016 is formed using the same conductive film as source electrode layers and drain electrode layers of the transistors 4010 and 4011.

The connection terminal electrode 4015 is electrically connected to a terminal included in the FPC 4018 through an anisotropic conductive film 4019.

Although FIGS. 4A1 and 4A2 illustrate an example in which the signal line driver circuit 4003 or the signal line driver circuit 4003a is formed separately and mounted on the first substrate 4001, one embodiment of the present invention is not limited to this structure. The scanning line driver circuit may be separately formed and then mounted, or only part of the signal line driver circuit or part of the scanning line driver circuit may be separately formed and then mounted.

As above, with the use of the liquid crystalline compound (PPEP-nFCNF (n is an integer of 2 to 10) (abbreviation)) or the liquid crystal composition, a liquid crystal element or a liquid crystal display device which achieves higher contrast can be provided. Thus, a liquid crystal display device with high visibility and high image quality can be provided.

Since a liquid crystal composition including the liquid crystalline compound (PPEP-nFCNF (n is an integer of 2 to 10) (abbreviation)) and exhibiting a blue phase is capable of high-speed response, a high-performance liquid crystal display device can be achieved.

This embodiment can be implemented in appropriate combination with any of the structures described in the other embodiments.

Embodiment 4

A liquid crystal display device disclosed in this specification can be applied to a variety of electronic devices (including game machines). Examples of electronic devices are a television, set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a portable information terminal, an audio reproducing device, a large-sized game machine such as a pachinko machine, and the like.

FIG. 5A illustrates a laptop personal computer, which includes a main body 3001, a housing 3002, a display portion 3003, a keyboard 3004, and the like. The liquid crystal display device described in any of Embodiments 1 to 3 is used for the display portion 3003, whereby a laptop personal computer with high contrast, excellent visibility, and high reliability can be provided.

FIG. 5B illustrates a personal digital assistant (PDA), which includes a main body 3021 provided with a display portion 3023, an external interface 3025, operation buttons 3024, and the like. A stylus 3022 is provided as an accessory for operation. The liquid crystal display device described in any of Embodiments 1 to 3 is used for the display portion 3023, whereby a personal digital assistant (PDA) with high contrast, excellent visibility, and high reliability can be provided.

FIG. 5C illustrates an e-book reader, which includes two housings, a housing 2701 and a housing 2703. The housing 2701 and the housing 2703 are combined with a hinge 2711 so that the e-book reader can be opened and closed with the hinge 2711 as an axis. With such a structure, the e-book reader can operate like a paper book.

A display portion 2705 and a display portion 2707 are incorporated in the housing 2701 and the housing 2703, respectively. The display portion 2705 and the display portion 2707 may display one image or different images. In the structure where different images are displayed in the above display portions, for example, the right display portion (the display portion 2705 in FIG. 5C) can display text and the left display portion (the display portion 2707 in FIG. 5C) can display images. The liquid crystal display device described in any of Embodiments 1 to 3 is used for the display portions 2705 and 2707, whereby an e-book reader with high contrast, excellent visibility, and high reliability can be provided. In the case of using a transflective or reflective liquid crystal display device as the display portion 2705, the e-book reader may be used in a comparatively bright environment; therefore, a solar cell may be provided so that power generation by the solar cell and charge by a battery can be performed. When a lithium ion battery is used as the battery, there are advantages of downsizing and the like.

FIG. 5C illustrates an example in which the housing 2701 is provided with an operation portion and the like. For example, the housing 2701 is provided with a power switch 2721, operation keys 2723, a speaker 2725, and the like. With the operation keys 2723, pages can be turned. Note that a keyboard, a pointing device, or the like may also be provided on the surface of the housing, on which the display portion is provided. Furthermore, an external connection terminal (an earphone terminal, a USB terminal, or the like), a recording medium insertion portion, and the like may be provided on the back surface or the side surface of the housing. Further, the e-book reader may have a function of an electronic dictionary.

The e-book reader may transmit and receive data wirelessly. Through wireless communication, desired book data or the like can be purchased and downloaded from an electronic book server.

FIG. 5D illustrates a mobile phone, which includes two housings, a housing 2800 and a housing 2801. The housing 2801 includes a display panel 2802, a speaker 2803, a microphone 2804, a pointing device 2806, a camera lens 2807, an external connection terminal 2808, and the like. In addition, the housing 2800 includes a solar cell 2810 having a function of charge of the mobile phone, an external memory slot 2811, and the like. An antenna is, incorporated in the housing 2801. The liquid crystal display device described in any of Embodiments 1 to 3 is used for the display panel 2802, whereby a mobile phone with high contrast, excellent visibility, and high reliability can be provided.

Further, the display panel 2802 is provided with a touch panel. A plurality of operation keys 2805 which is displayed as images is illustrated by dashed lines in FIG. 5D. Note that a boosting circuit by which a voltage output from the solar cell 2810 is increased to be sufficiently high for each circuit is also provided.

The display direction of the display panel 2802 is changed as appropriate depending on a usage pattern. Further, the camera lens 2807 is provided on the same surface as the display panel 2802, so that the mobile phone can be used as a video phone. The speaker 2803 and the microphone 2804 can be used for videophone calls, recording and playing sound, and the like as well as voice calls. Furthermore, the housings 2800 and 2801 which are developed as illustrated in FIG. 5D can overlap with each other by sliding; thus, the size of the mobile phone can be decreased, which makes the mobile phone suitable for being carried.

The external connection terminal 2808 can be connected to an AC adapter and various types of cables such as a USB cable, and charging and data communication with a personal computer are possible. Moreover, a large amount of data, can be stored by inserting a storage medium into the external memory slot 2811 and can be moved.

Further, in addition to the above functions, an infrared communication function, a television reception function, or the like may be provided.

FIG. 5E illustrates a digital video camera, which includes a main body 3051, a display portion A 3057, an eyepiece 3053, an operation switch 3054, a display portion B 3055, a battery 3056, and the like. The liquid crystal display device described in any of Embodiments 1 to 3 is used for the display portion A 3057 and the display portion B 3055, whereby a digital video camera with high contrast, excellent visibility, and high reliability can be provided.

FIG. 5F illustrates a television set, which includes a housing 9601, a display portion 9603, and the like. The display portion 9603 can display images. Here, the housing 9601 is supported by a stand 9605. The liquid crystal display device described in any of Embodiments 1 to 3 is used for the display portion 9603, whereby a television set with high contrast, excellent visibility, and high reliability can be provided.

The television set can operate with an operation switch of the housing 9601 or a separate remote control device. Further, the remote controller may be provided with a display portion for displaying data output from the remote controller.

Note that the television set is provided with a receiver, a modem, and the like. With the use of the receiver, general television broadcasting can be received. Moreover, when the display device is connected to a communication network with or without wires via the modem, one-way (from a sender to a receiver) or two-way (between a sender and a receiver or between receivers) data communication can be performed.

This embodiment can be implemented in appropriate combination with any of the structures described in the other embodiments.

Example 1

In this example, an example of synthesizing 4-(4-n-propylphenyl)benzoic acid 4-cyano-3,5-difluorophenyl (abbreviation: PPEP-3FCNF) represented by the structural formula (103) in Embodiment 1 will be described.

Synthesis method of 4-(4-n-propylphenyl)benzoic acid 4-cyano-3,5-difluorophenyl (abbreviation: PPEP-3FCNF))

A synthetic scheme of PPEP-3FCNF (abbreviation) represented by the structural formula (103) is shown in (B-1) below.

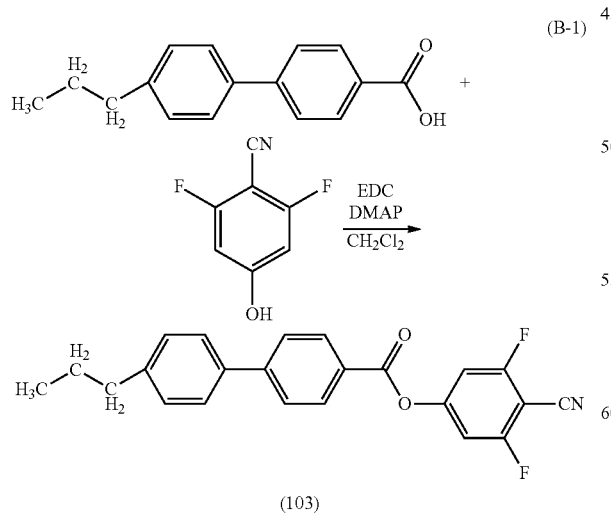

(B-1)

(103)

Into a 50-mL recovery flask were put 2.4 g (10 mmol) of 4-(4-n-propylphenyl)benzoic acid, 1.6 g (10 mmol) of 2,6-difluoro-4-hydroxybenzonitrile, 0.18 g (1.5 mmol) of 4-dimethylaminopyridine, and 10 mL of dichloromethane, and stirring was performed. To this mixture, 2.2 g (11 mmol) of 1-ethyl-3-(3-dimethylaminopropyl)carbodiimide hydrochloride (EDC) was added, and stirring was performed in the air at room temperature for 24 hours. After predetermined time passed, water was added to the obtained mixture to extract an aqueous layer of this mixture with dichloromethane. The obtained extracted solution and an organic layer were combined and washed with a saturated aqueous solution of sodium hydrogen carbonate and saturated saline, and then, the mixture was dried with magnesium sulfate. The mixture was gravity filtered, and the obtained filtrate was condensed to give a yellow solid. This solid was purified by silica gel column chromatography (developing solvent: chloroform). The obtained fraction was concentrated to give a yellow solid. This solid was purified by high performance liquid chromatography (HPLC) (developing solvent: chloroform). The obtained fraction was concentrated to give 3.5 g of a white solid, which was a target substance, in a yield of 93%.

Further, 1.6 g of the obtained white solid was purified by distillation, whereby 1.5 g of a white solid, which was a target substance, was obtained in a yield of 94%.

This compound was identified by a nuclear magnetic resonance method (NMR) as 4-(4-n-propylphenyl)benzoic acid 4-cyano-3,5-difluorophenyl (PPEP-3FCNF) which was a target substance.

Figure 8A:
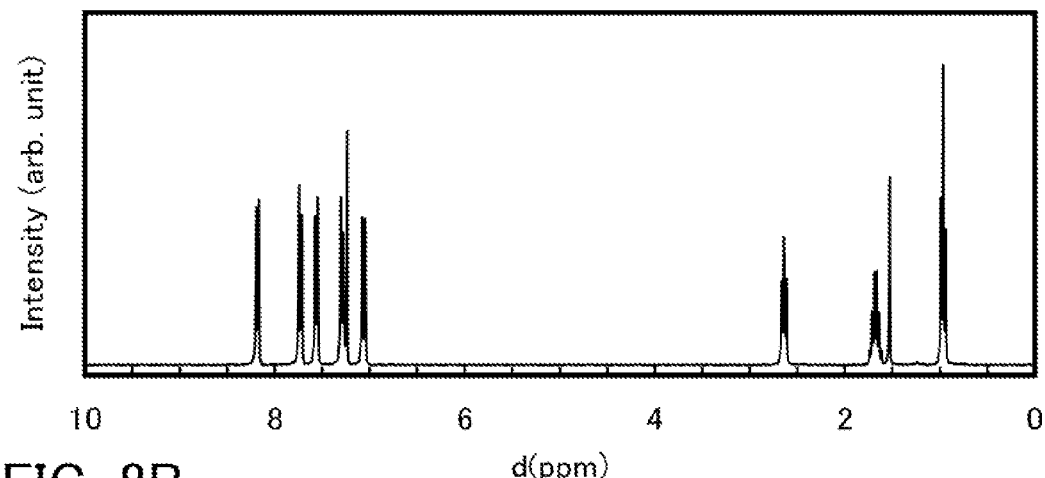
FIGS. 8A to 8C are $^1$H NMR charts of PPEP-3FCNF.
Figure 8B:
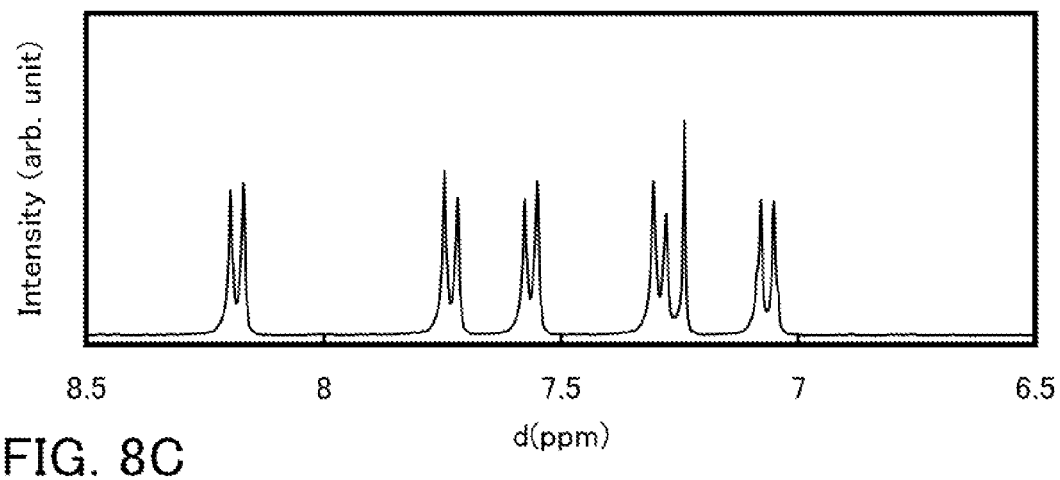
Figure 8C:
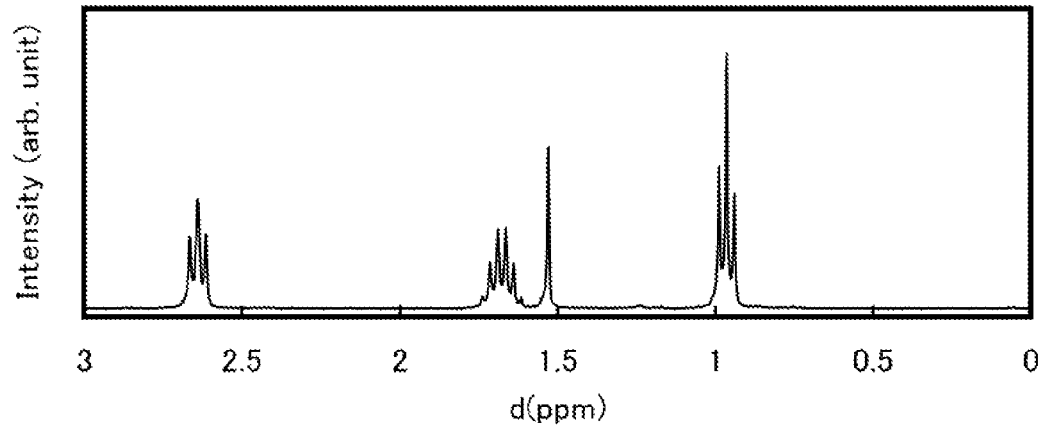

The $^1$H NMR data of the obtained substance (PPEP-3FCNF) is as follows. $^1$H NMR (CDCl$_3$, 300 MHz): δ (ppm)= 0.96 (t, 3H), 1.62-1.74 (m, 2H), 2.64 (t, 2H), 7.07 (d, 2H), 7.29 (d, 2H), 7.56 (d, 2H), 7.73 (d, 2H), 8.18 (d, $21^{-1}$). FIGS. 8A to 8C are $^1$H NMR charts. Note that FIG. 8B is an enlarged chart showing the range of 6.5 ppm to 8.5 ppm in FIG. 8A. Note also that FIG. 8C is an enlarged chart showing the range of 0.0 ppm to 3.0 ppm in FIG. 8A.

Example 2

In this example, an example of synthesizing 4-(4-n-pentylphenyl)benzoic acid 4-cyano-3,5-difluorophenyl (abbreviation: PPEP-5FCNF) represented by the structural formula (105) in Embodiment 1 will be described:

Synthesis method of 4-(4-n-pentylphenyl)benzoic acid 4-cyano-3,5-difluorophenyl (abbreviation: PPEP-5FCNF))

A synthetic scheme of PPEP-5FCNF (abbreviation) represented by the structural formula (105) is shown in (A-1) below.

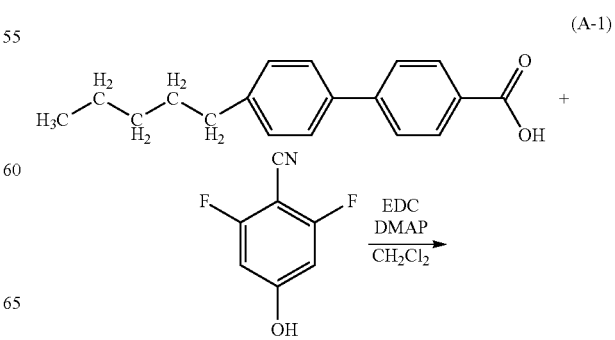

(A-1)

(105)

Into a 50-mL recovery flask were put 2.3 g (8.6 mmol) of 4-(4-n-pentylphenyl)benzoic acid, 1.3 (8.4 mmol) of 2,6-difluoro-4-hydroxybenzonitrile, 0.16 g (1.3 mmol) of 4-dimethylaminopyridine, and 8.6 mL of dichloromethane, and stirring was performed. To this mixture, 1.8 g (9.4 mmol) of 1-ethyl-3-(3-dimethylaminopropyl)carbodiimide hydrochloride (EDC) was added, and stirring was performed in the air at room temperature for 18 hours. After predetermined time passed, water was added to the obtained mixture to extract an aqueous layer with dichloromethane. The obtained extracted solution and an organic layer were combined and washed with a saturated aqueous solution of sodium hydrogen carbonate and saturated saline, and then, the mixture was dried with magnesium sulfate. The mixture was gravity filtered, and the obtained filtrate was condensed to give a light brown solid. This solid was purified by silica gel column chromatography (developing solvent: toluene). The obtained fraction was concentrated to give a yellow solid. This solid was purified by high performance liquid chromatography (HPLC) (developing solvent: chloroform). The obtained fraction was concentrated to give 2.7 g of a white solid, which was a target substance, in a yield of 79%.

Further, 2.7 g of the obtained white solid was purified by distillation, whereby 2.5 g of a white solid, which was a target substance, was obtained in a yield of 93%.

This compound was identified by a nuclear magnetic resonance method (NMR) as 4-(4-n-pentylphenyl)benzoic acid 4-cyano-3,5-difluorophenyl (PPEP-5FCNF) which was a target substance.

Figure 9A:
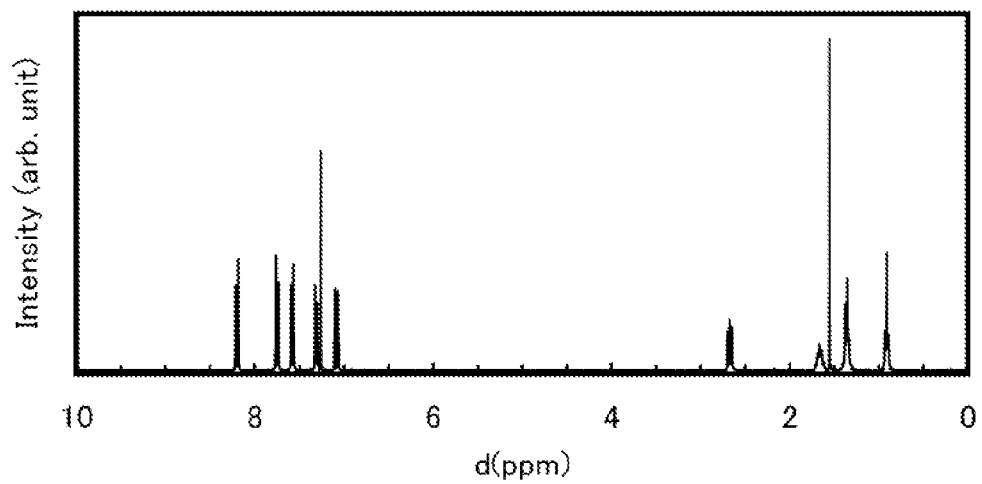
FIGS. 9A to 9C are $^1$H NMR charts of PPEP-5FCNF.
Figure 9B:
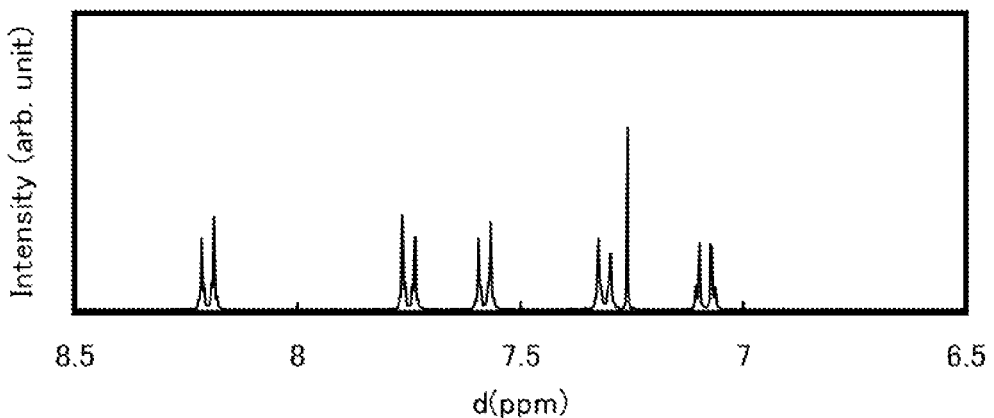
Figure 9C:
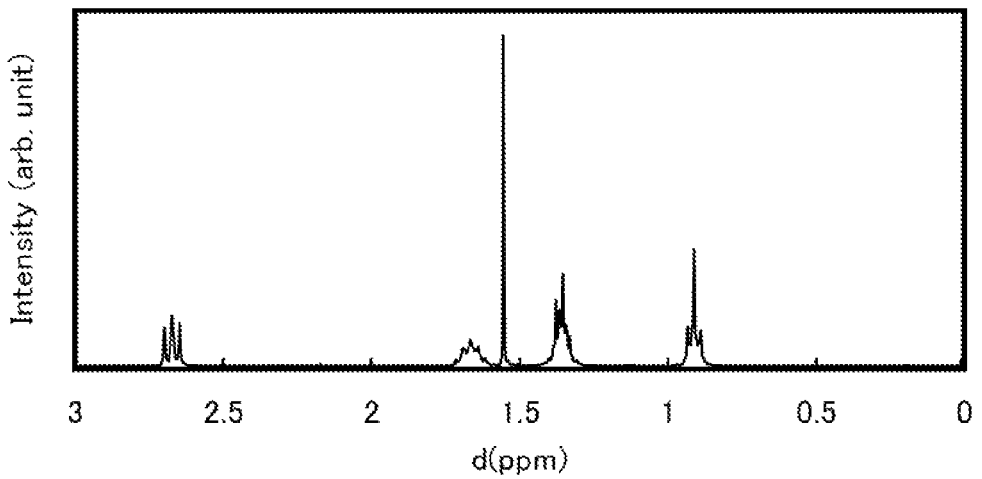

The $^1$H NMR data of the obtained substance is as follows. $^1$H NMR (CDCl$_3$, 300 MHz): δ (ppm)=0.91 (t, 3H), 1.31-1.40 (On, 4H), 1.62-1.72 (m, 2H), 2.67 (t, 2H), 7.09 (d, 2H), 7.31 (d, 2H), 7.58 (d, 2H), 7.75 (d, 2H), 8.20 (d, 2H). FIGS. 9A to 9C are $^1$H NMR charts. Note that FIG. 9B is an enlarged chart showing the range of 6.5 ppm to 8.5 ppm in FIG. 9A. Note also that FIG. 9C is an enlarged chart showing the range of 0.0 ppm to 3.0 ppm in FIG. 9A.

Example 3

In this example, an example of synthesizing 4-(4-n-heptylphenyl)benzoic acid 4-cyano-3,5-difluorophenyl (abbreviation: PPEP-7FCNF) represented by the structural formula (107) in Embodiment 1 will be described.

Synthesis method of 4-(4-n-heptylphenyl)benzoic acid 4-cyano-3,5-difluorophenyl (abbreviation: PPEP-7FCNF))

A synthetic scheme of PPEP-7FCNF (abbreviation) represented by the structural formula (107) is shown in (C-1) below.

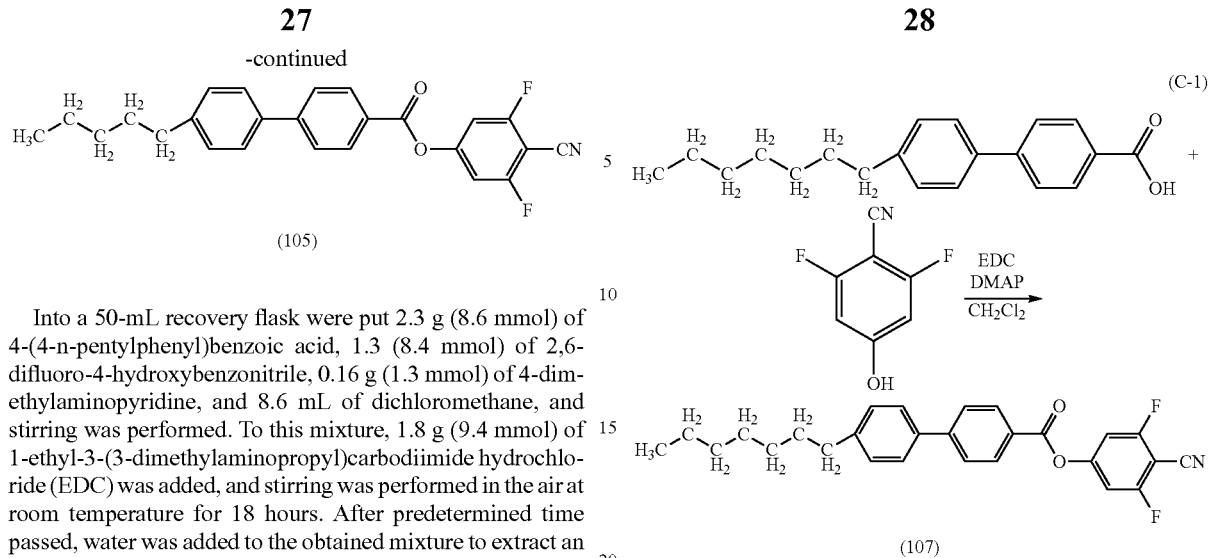

(C-1)

(107)

Into a 50-mL recovery flask were put 2.0 g (6.7 mmol) of 4-(4-n-heptylphenyl)benzoic acid, 1.0 g (6.4 mmol) of 2,6-difluoro-4-hydroxybenzonitrile, 0.12 g (0.98 mmol) of 4-dimethylaminopyridine, and 6.7 mL of dichloromethane, and stirring was performed. To this mixture, 1.4 g (7.3 mmol) of 1-ethyl-3-(3-dimethylaminopropyl)carbodiimide hydrochloride (EDC) was added, and stirring was performed in the air at room temperature for 24 hours. After predetermined time passed, water was added to the obtained mixture to extract an aqueous layer of this mixture with dichloromethane. The obtained extracted solution and an organic layer were, combined and washed with a saturated aqueous solution of sodium hydrogen carbonate and saturated saline; and then, the mixture was dried with magnesium sulfate. The mixture was gravity filtered, and the obtained filtrate was condensed to give a white solid. This solid was purified by silica gel column chromatography (developing solvent: toluene). The obtained fraction was concentrated to give a white solid. This solid was purified by high performance liquid chromatography (HPLC) (developing solvent: chloroform). The obtained fraction was concentrated to give 2.3 g of a white solid, which was a target substance, in a yield of 79%.

Further, 1.4 g of the obtained white solid was purified by distillation, whereby 1.2 g of a white solid, which was a target substance, was obtained in a yield of 86%.

This compound was identified by a nuclear magnetic resonance method (NMR) as 4-(4-n-heptylphenyl)benzoic acid 4-cyano-3,5-difluorophenyl (PPEP-7FCNF) which was a target substance.

Figure 10A:
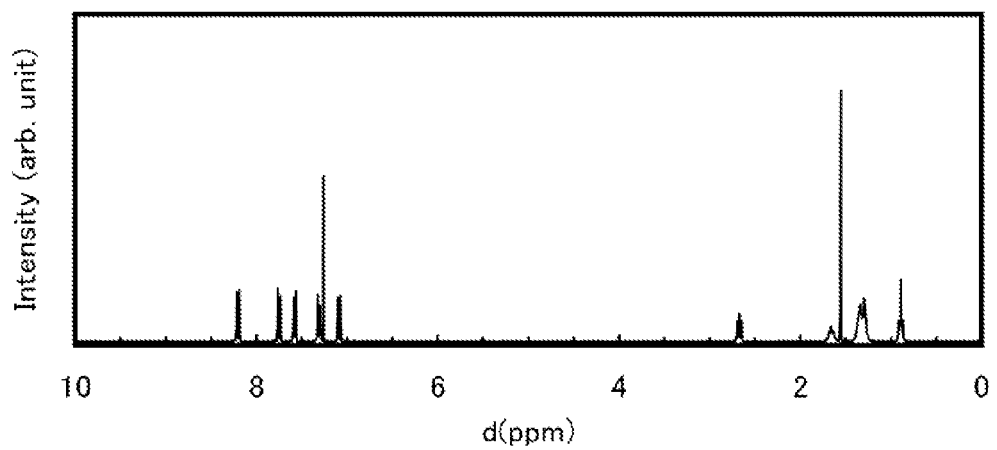
FIGS. 10A to 10C are $^1$H NMR charts of PPEP-7FCNF.
Figure 10B:
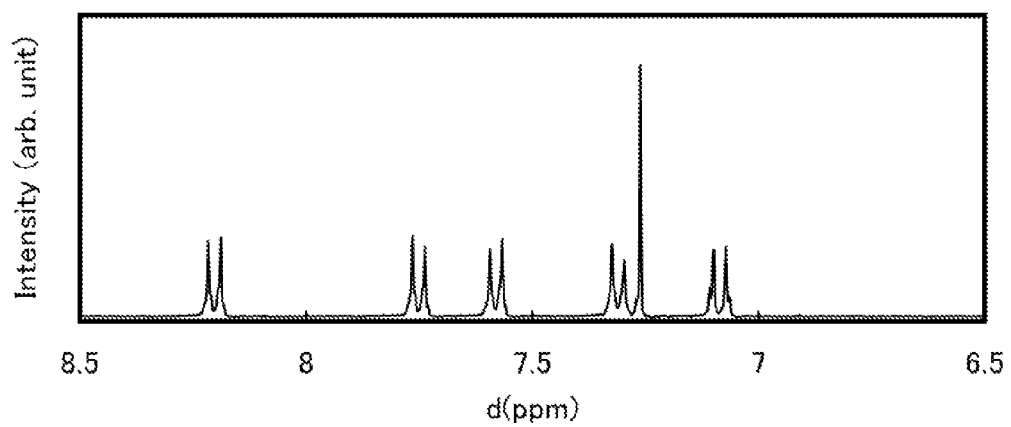
Figure 10C:
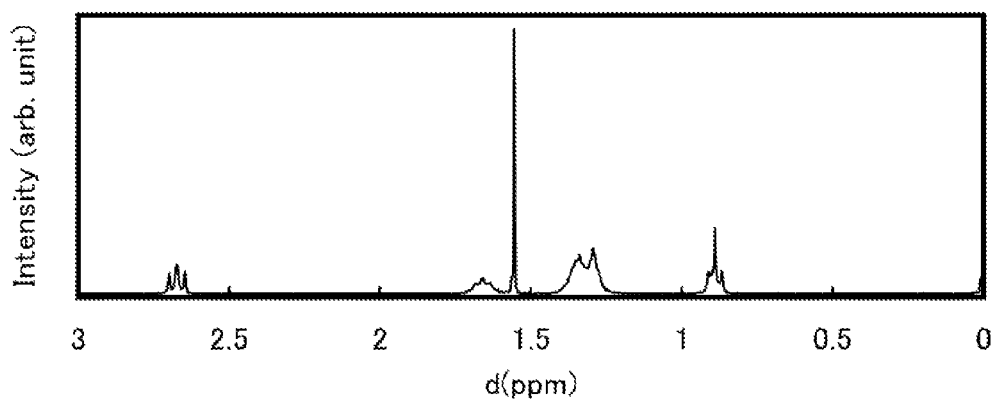

The $^1$H NMR data of the obtained substance (PPEP-7FCNF) is as follows. $^1$H NMR (CDCl$_3$, 300 MHz): δ (ppm)= 0.89 (t, 3H), 1.30-1.34 (m, 8H), 1.63-1.69 (m, 2H), 2.67 (t, 2H), 7.09 (d, 2H), 7.31 (d, 2H), 7.58 (d, 2H), 7.75 (d, 2H), 8.20 (d, 2H). FIGS. 10A to 10C are $^1$H NMR charts. Note that FIG. 10B is an enlarged chart showing the range of 6.5 ppm to 8.5 ppm in FIG. 10A. Note also that FIG. 10C is an enlarged chart showing the range of 0.0 ppm to 3.0 ppm in FIG. 10A.

Example 4

In this example, an example of synthesizing 4-(4-n-nonylphenyl)benzoic acid 4-cyano-3,5-difluorophenyl (abbreviation: PPEP-9FCNF) represented by the structural formula (109) in Embodiment 1 will be described.

Synthesis method of 4-(4-n-nonylphenyl)benzoic acid 4-cyano-3,5-di fluorophenyl (abbreviation: PPEP-9FCNF))

A synthetic scheme of PPEP-9FCNF (abbreviation) represented by the structural formula (109) is shown in (D-1) below.

This compound was identified by a nuclear magnetic resonance method (NMR) as 4-(4-n-nonylphenyl)benzoic acid 4-cyano-3,5-difluorophenyl (PPEP-9FCNF) which was a target substance.

The $^1$H NMR data of the obtained substance (PPEP-9FCNF) is as follows. $^1$H NMR (CDCl$_3$, 300 MHz): δ (ppm)= 0.88 (t, 3H), 1.24-1.33 (m, 12H), 1.60-1.68 (m, 2H), 2.07 (t,

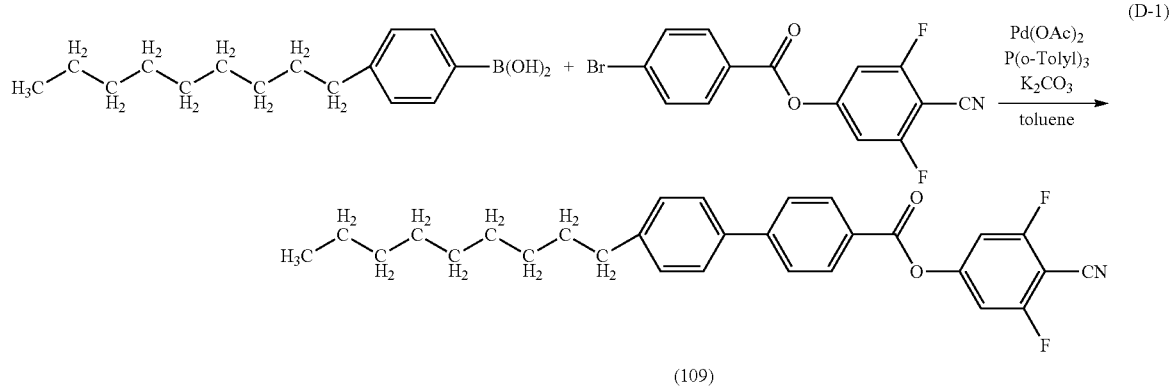

(109)

Into a 50-mL three-neck flask were put 1.3 g (5.2 mmol) of (4-n-nonylphenyl)boronic acid, 1.7 g (5.0 mmol) of 4-bromo benzoic acid 4-cyano-3,5-difluorophenyl, 77 mg (0.25 mmol) of tris(2-methylphenyl)phosphine, and 1.4 g (0.010 mol) of potassium carbonate, and the air in the flask was replaced with nitrogen. To the mixture, 5.1 mL of toluene was added, and this mixture was degassed by being stirred under reduced pressure. Then, 11 mg (0.050 mmol) of palladium(II) acetate was added to this mixture, and the mixture was stirred at 90° C. for 24 hours. After predetermined time passed, an aqueous layer of the obtained mixture was extracted with toluene. The obtained extracted solution and an organic layer were combined and washed with saturated saline, and then, the mixture was dried with magnesium sulfate. The mixture was separated by gravity filtration, and the obtained filtrate was condensed to give a yellow oily substance. This oily substance was purified by silica gel column chromatography (developing solvent: hexane and ethyl acetate (hexane:ethyl acetate=5:1)). The obtained fraction was concentrated to give a yellow oily substance. This oily substance was purified by high performance liquid chromatography (HPLC) (developing solvent: chloroform). The obtained fraction was concentrated to give 0.88 g of a yellow oily substance, which was a target substance, in a yield of 38%.

Figure 11A:
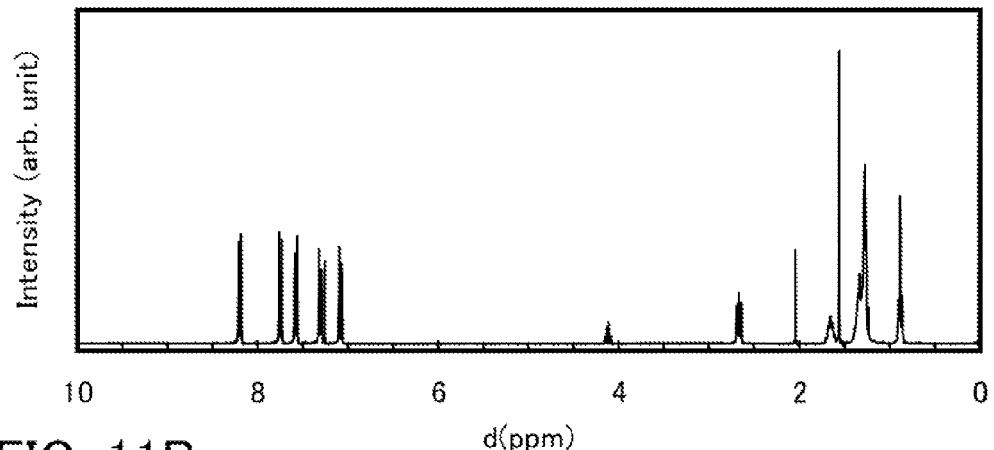
FIGS. 11A to 11C are $^1$H NMR charts of PPEP-9FCNF.
Figure 11B:
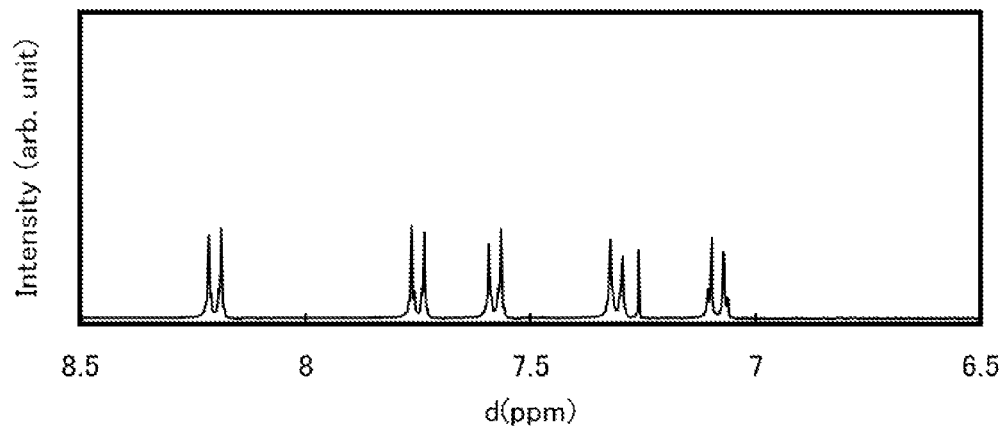
Figure 11C:
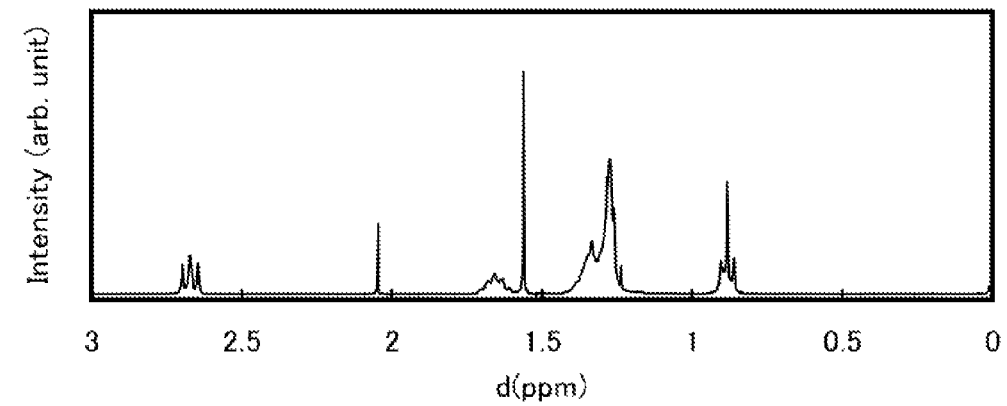

2H), 7.08 (d, 2H), 7.31 (d, 2H), 7.58 (d, 2H), 7.75 (d, 2H), 8.20 (d, 2H). FIGS. 11A to 11C are $^1$H NMR charts. Note that FIG. 11B is an enlarged chart showing the range of 6.5 ppm to 8.5 ppm in FIG. 11A. Note also that FIG. 11C is an enlarged chart showing the range of 0.0 ppm to 3.0 ppm in FIG. 11A.

Example 5

In this example, an example of synthesizing 4-(4-n-undecylphenyl)benzoic acid 4-cyano-3,5-difluorophenyl (abbreviation: PPEP-11FCNF) represented by the structural formula (111) in Embodiment 1 will be described.

Synthesis method of 4-(4-n-undecylphenyl)benzoic acid 4-cyano-3,5-difluorophenyl (abbreviation: PPEP-11FCNF))

A synthetic scheme of PPEP-11FCNF (abbreviation) represented by the structural formula (111) is shown in (E-1) below.

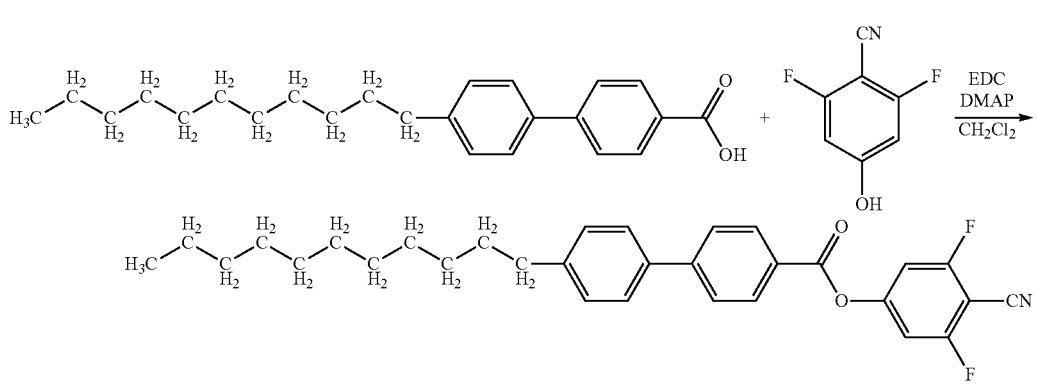

Into a 50-mL recovery flask were put 2.0 g (5.7 mmol) of 4-(4-n-undecylphenyl)benzoic acid, 0.88 g (5.7 mmol) of 2,6-difluoro-4-hydroxybenzonitrile, 0.11 g (0.90 mmol) of 4-(N,N-dimethyl)aminopyridine, and 5.7 mL of dichloromethane, and stirring was performed. To this mixture, 1.2 g (6.3 mmol) of 1-ethyl-3-(3-dimethylaminopropyl)carbodiimide hydrochloride (EDC) was added, and stirring was performed in the air at room temperature for 24 hours. After predetermined time passed, water was added to the obtained mixture to extract an aqueous layer of this mixture with dichloromethane. The obtained extracted solution and an organic layer were combined and washed with a saturated aqueous solution of sodium hydrogen carbonate and saturated saline, and then, the mixture was dried with magnesium sulfate. The mixture was gravity filtered, and the obtained filtrate was condensed to give a white solid. This solid was purified by silica gel column chromatography (developing solvent: toluene). The obtained fraction was concentrated to give a white solid. This solid was purified by high performance liquid column chromatography (HPLC) (developing solvent: chloroform). The obtained fraction was concentrated to give 1.7 g of a white solid, which was a target substance, in a yield of 61%.

This compound was identified by a nuclear magnetic resonance method (NMR) as 4-(4-n-undecylphenyl)benzoic acid 4-cyano-3,5-difluorophenyl (PPEP-11FCNF) which was a target substance.

Figure 12A:
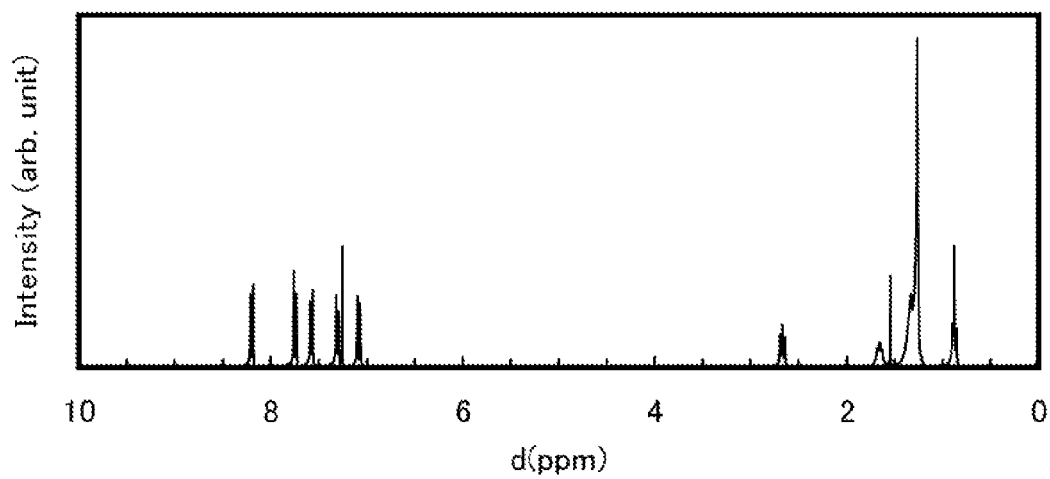
FIGS. 12A to 12C are $^1$H NMR charts of PPEP-11FCNF.
Figure 12B:
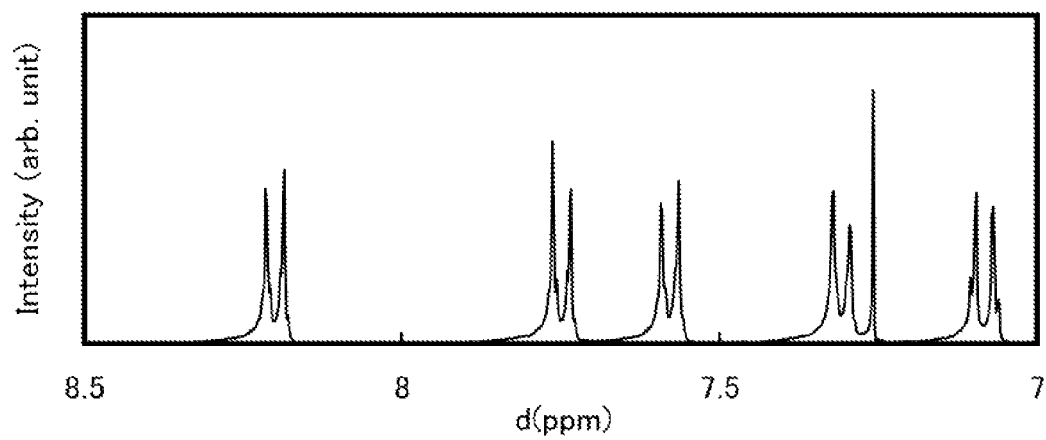
Figure 12C:
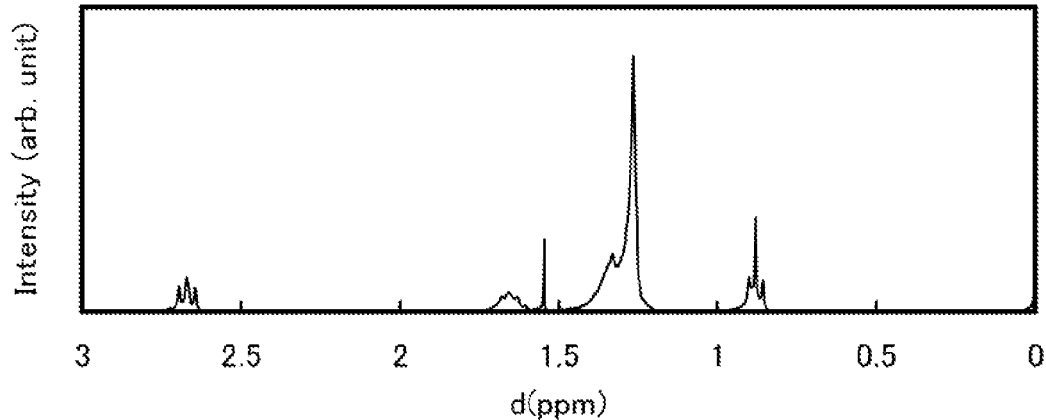

The $^1$H NMR data of the obtained substance (PPEP-11FCNF) is as follows. $^1$H NMR (CDCl$_3$, 300 MHz): δ (ppm)=0.88 (t, 3H), 1.27-1.33 (m, 16H), 1.63-1.68 (m, 2H), 2.67 (t, 2H), 7.08 (d, 2H), 7.31 (d, 2H), 7.58 (d, 2H), 7.75 (d, 2H), 8.20 (d, 2H). FIGS. 12A to 12C are $^1$H NMR charts. Note that FIG. 12B is an enlarged chart showing the range of 7.0 ppm to 8.5 ppm in FIG. 12A. Note also that FIG. 12C is an enlarged chart showing the range of 0.0 ppm to 3.0 ppm in FIG. 12A.

Example 6

In this example, liquid crystal elements (Liquid Crystal Elements 1 to 5) which include a liquid crystal composition including the liquid crystalline compound according to one embodiment of the present invention described in Examples 1 to 5 and a comparative liquid crystal element which does not include the liquid crystalline compound according to one embodiment of the present invention were manufactured, and characteristics thereof were evaluated.

Tables 1 to 5 show structures of liquid crystal compositions used for Liquid Crystal Elements 1 to 5 manufactured in this example. Table 6 shows a structure of a liquid crystal composition used for the comparative liquid crystal element. In Tables 1 to 6, the mixture ratios are all represented in weight ratios.

TABLE 1

| Components of Liquid Crystal Element 1 | | Weight (mg) | Proportion (wt %) |
|---|---|---|---|
| Liquid Crystal 1 | MDA-00-3506 | 71.4 | 24.74 |
| Liquid Crystal 2 | NEDO LC-C | 47.5 | 16.46 |
| Liquid Crystal 3 | CPP-3FF | 47.8 | 16.55 |
| Liquid Crystal 4 | PEP-5CNF | 36.5 | 12.64 |
| Liquid Crystal 5 | PPEP-3FCNF | 35.9 | 12.44 |
| Chiral Agent | ISO-(6OBA)$_2$ | 25.5 | 8.83 |
| Polymerizable Monomers | RM257 | 11.5 | 3.98 |
|  | DMeAc | 11.3 | 3.91 |
| Polymerization Initiator | DMPAP | 1.3 | 0.45 |
| Total |  | 288.7 | 100.00 |

TABLE 2

| Components of Liquid Crystal Element 2 | | Weight (mg) | Proportion (wt %) |
|---|---|---|---|
| Liquid Crystal 1 | MDA-00-3506 | 152.89 | 24.78 |
| Liquid Crystal 2 | NEDO LC-C | 101.83 | 16.50 |
| Liquid Crystal 3 | CPP-3FF | 102.24 | 16.57 |
| Liquid Crystal 4 | PEP-5CNF | 76.44 | 12.39 |
| Liquid Crystal 5 | PPEP-5FCNF | 77.6 | 12.58 |
| Chiral Agent | ISO-(6OBA)$_2$ | 53.8 | 8.72 |
| Polymerizable Monomers | RM257 | 24.8 | 4.02 |
|  | DMeAc | 24.5 | 3.97 |
| Polymerization Initiator | DMPAP | 2.9 | 0.47 |
| Total |  | 617.00 | 100.00 |

TABLE 3

| Components of Liquid Crystal Element 3 | | Weight (mg) | Proportion (wt %) |
|---|---|---|---|
| Liquid Crystal 1 | MDA-00-3506 | 70.2 | 24.71 |
| Liquid Crystal 2 | NEDO LC-C | 46.7 | 16.45 |
| Liquid Crystal 3 | CPP-3FF | 46.9 | 16.53 |
| Liquid Crystal 4 | PEP-5CNF | 35.9 | 12.63 |
| Liquid Crystal 5 | PPEP-7FCNF | 35.6 | 12.54 |
| Chiral Agent | ISO-(6OBA)$_2$ | 24.8 | 8.73 |
| Polymerizable Monomers | RM257 | 11.4 | 4.01 |
|  | DMeAc | 11.1 | 3.91 |
| Polymerization Initiator | DMPAP | 1.4 | 0.49 |
| Total |  | 284.0 | 100.00 |

TABLE 4

| Components of Liquid Crystal Element 4 | | Weight (mg) | Proportion (wt %) |
|---|---|---|---|
| Liquid Crystal 1 | MDA-00-3506 | 70.4 | 24.79 |
| Liquid Crystal 2 | NEDO LC-C | 46.9 | 16.50 |
| Liquid Crystal 3 | CPP-3FF | 47.1 | 16.58 |
| Liquid Crystal 4 | PEP-5CNF | 36.0 | 12.66 |
| Liquid Crystal 5 | PPEP-9FCNF | 35.1 | 12.36 |
| Chiral Agent | ISO-(6OBA)$_2$ | 24.9 | 8.77 |
| Polymerizable Monomers | RM257 | 11.4 | 4.01 |
|  | DMeAc | 11.1 | 3.91 |
| Polymerization Initiator | DMPAP | 1.2 | 0.42 |
| Total |  | 284.0 | 100.00 |

TABLE 5

| Components of Liquid Crystal Element 5 | | Weight (mg) | Proportion (wt %) |
|---|---|---|---|
| Liquid Crystal 1 | MDA-00-3506 | 70.6 | 24.91 |
| Liquid Crystal 2 | NEDO LC-C | 46.2 | 16.30 |
| Liquid Crystal 3 | CPP-3FF | 47.4 | 16.73 |
| Liquid Crystal 4 | PEP-5CNF | 36.1 | 12.74 |
| Liquid Crystal 5 | PPEP-11FCNF | 35.3 | 12.46 |
| Chiral Agent | ISO-(6OBA)$_2$ | 24.6 | 8.68 |
| Polymerizable Monomers | RM257 | 11.2 | 3.95 |
|  | DMeAc | 11.1 | 3.92 |
| Polymerization Initiator | DMPAP | 0.9 | 0.32 |
| Total |  | 283.4 | 100.00 |

TABLE 6

| Components of Comparative Liquid Crystal Element | | Weight (mg) | Proportion (wt %) |
|---|---|---|---|
| Liquid Crystal 1 | MDA-00-3506 | 139.40 | 24.81 |
| Liquid Crystal 2 | NEDO LC-C | 93.62 | 16.66 |
| Liquid Crystal 3 | CPP-3FF | 92.86 | 16.53 |
| Liquid Crystal 4 | PEP-5CNF | 139.92 | 24.90 |
| Chiral Agent | ISO-(6OBA)$_2$ | 48.8 | 8.68 |
| Polymerizable Monomers | RM257 | 23.1 | 4.11 |
|  | DMeAc | 72.3 | 3.97 |
| Polymerization Initiator | DMPAP | 1.9 | 0.34 |
| Total |  | 561.90 | 100.00 |

In Liquid Crystal Elements 1 to 5 and the comparative liquid crystal element, the following components were used: MDA-00-3506 (produced by Merck Ltd.) as Liquid Crystal 1; NEDO LC-C (produced by Merck Ltd.) as Liquid Crystal 2; 4-(trans-4-n-propylcyclohexyl)-3',4'-difluoro-1,1'-biphenyl (abbreviation: CPP-3 FF) (produced by Daily Polymer Corporation) as Liquid Crystal 3; 4-n-pentylbenzoic acid 4-cyano-3-fluorophenyl (abbreviation: PEP-5CNF) (produced by Daily Polymer Corporation) as Liquid Crystal 4; 1,4:3,6-dianhydro-2,5-bis[4-(n-hexyl-1-oxy)benzoic acid]sorbitol (abbreviation: ISO-(6OBA)$_2$) (produced by Midori Kagaku Co., Ltd.) as a chiral agent; dodecyl methacrylate (abbreviation: DMeAc) (produced by Tokyo Chemical industry Co., Ltd.) which is a non-liquid-crystalline UV polymerizable monomer and RM257 (produced by Merck Ltd.) which is a liquid crystalline UV polymerizable monomer as polymerizable monomers; and DMPAP (abbreviation) (produced by Tokyo Chemical Industry Co., Ltd.) as a polymerization initiator.

The structural formulae of CPP-3FF (abbreviation) as Liquid Crystal 3, PEP-5CNF (abbreviation) as Liquid Crystal 4, ISO-(6OBA)$_2$ (abbreviation) as the chiral agent, RM257 (produced by Merck Ltd.) and dodecyl methacrylate (DMeAc) (abbreviation) as the polymerizable monomers, and DMPAP (abbreviation) as the polymerization initiator, which were used in this example, are shown below.

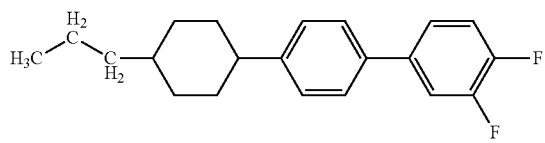

CPP-3FF

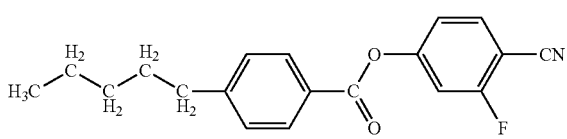

PEP-5CNF

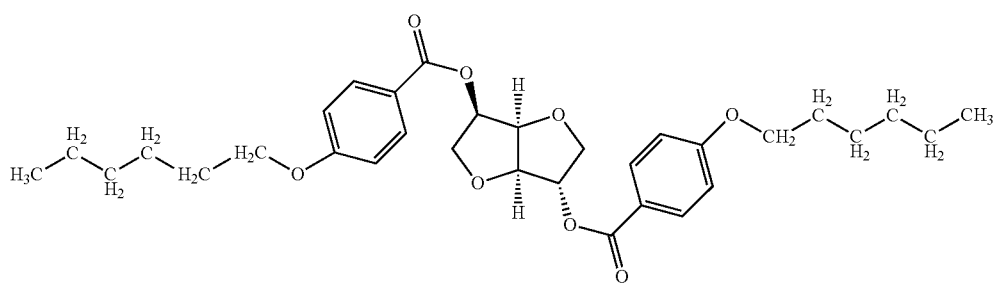

ISO-(6OBA)$_2$

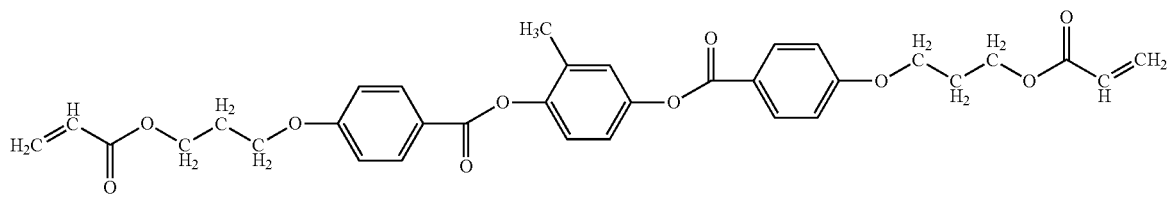

RM257

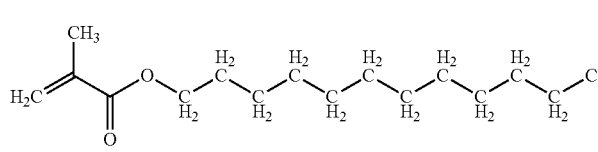

DMeAc

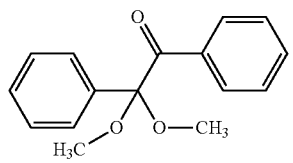

DMPAP

In Liquid Crystal Elements 1 to 5 shown in Tables 1 to 5, the following components were used as Liquid Crystal 5: a liquid crystal composition including PPEP-3FCNF (abbreviation) which is a liquid crystalline compound represented by the following structural formula (103), in Liquid Crystal Element 1; a liquid crystal composition including PPEP-5FCNF (abbreviation) which is a liquid crystalline compound represented by the following structural formula (105), in Liquid Crystal Element 2; a liquid crystal composition including PPEP-7FCNF (abbreviation) which is a liquid crystalline compound represented by the following structural formula (107), in Liquid Crystal Element 3; a liquid crystal composition including PPEP-9FCNF (abbreviation) which is a liquid crystalline compound represented by the following structural formula (109), in Liquid Crystal Element 4; and a liquid crystal composition including PPEP-11FCNF (abbreviation) which is a liquid crystalline compound represented by the following structural formula (111), in Liquid Crystal Element 5.

isotropic phase at ratios shown in Tables 1 to 5 was injected between the substrates by an injection method.

The pixel electrode layer and the common electrode layer were formed using indium tin oxide containing silicon oxide (ITSO) by a sputtering method. The thickness of each of the pixel electrode layer and the common electrode layer was 110 nm, the width thereof was 2 μm, and the distance between the pixel electrode layer and the common electrode layer was 2 μm. Further, an ultraviolet light and heat curable sealant was used as the sealant. As curing treatment, ultraviolet (irradiance of 100 mW/cm$^2$) irradiation was performed for 90 seconds, and then, heat treatment was performed at 120° C. for 1 hour.

Before polymer stabilization treatment, the liquid crystal compositions of Liquid Crystal Elements 1 to 5 and the comparative liquid crystal element were made to exhibit an isotropic phase through heat treatment. Then, Liquid Crystal Elements 1 to 5 and the comparative liquid crystal element

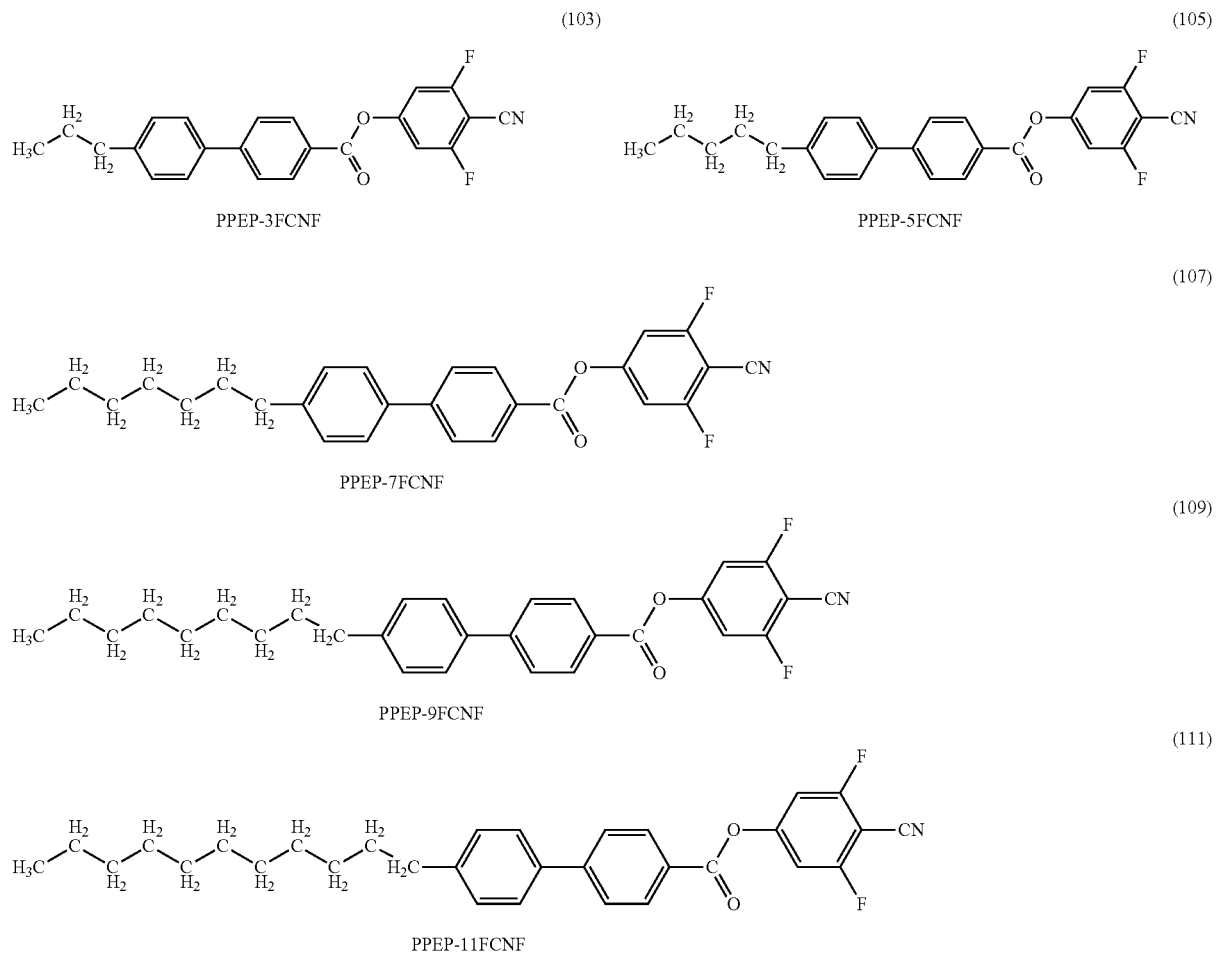

Liquid Crystal Elements 1 to 5 and the comparative liquid crystal element were each manufactured in such a manner that a glass substrate over which a pixel electrode layer and a common electrode layer were formed in comb-like shapes as in FIG. 3D and a glass substrate serving as a counter substrate were bonded to each other using sealant with a space (4 μm) provided therebetween and then a liquid crystal composition obtained by mixing materials in Tables 1 to 5 stirred in an were observed with the polarizing microscope while the temperature, was decreased by 1.0° C. per minute with the temperature controller. In this manner, the temperature range where the liquid crystal compositions exhibit a blue phase was measured. For the measurement, polarizing microscopes (MX-50 produced by Olympus Corporation (Liquid Crystal Elements 2 and 5 and the comparative liquid crystal element), MX61L produced by Olympus Corporation (Liquid Crystal Elements 1, 3, and 4), and a temperature controller (HCS302-MK1000 produced by Instec, Inc.) were used.

Further, each of Liquid Crystal Elements 1 to 5 and the comparative liquid crystal element was set at arbitrary constant temperature within the temperature range where a blue phase was exhibited, and irradiation with ultraviolet light (wavelength: 365 nm, irradiance: 1.5 mW/cm$^2$ (Liquid Crystal Elements 1 to 4 and the comparative liquid crystal element), wavelength: 365 nm, irradiance: 10 mW/cm$^2$ (Liquid Crystal Element 5)) was performed for 30 minutes. In such a manner, polymer stabilization treatment was performed.

As before the polymer stabilization treatment, after the polymer stabilization treatment, the liquid crystal compositions of Liquid Crystal Elements 1 to 5 and the comparative liquid crystal element were made to exhibit an isotropic phase through heat treatment. Then, Liquid Crystal Elements 1 to 5 and the comparative liquid, crystal element were observed with the polarizing microscope while the temperature was decreased by 1.0° C. per minute with the temperature controller. In this manner, the temperature range where the liquid crystal compositions exhibit a blue phase was measured.

The measurement conditions of the observation were as follows. In the polarizing microscope, a measurement mode was a reflective mode; polarizers were in crossed nicols; and the magnification was 200 times.

The temperature range where a blue phase is exhibited before the polymer stabilization treatment and the temperature range where a blue phase is exhibited after the polymer stabilization treatment of each of Liquid Crystal Elements 1 to 5 and the comparative liquid crystal element are shown in Table 7.

TABLE 7

| | Temperature Rang where Blue Phase is Exhibited | | | |
|---|---|---|---|---|
| | Before Polymer Stabilization Treatment | | After Polymer Stabilization Treatment | |
| Samples | Upper Limit (° C.) | Lower Limit (° C.) | Upper Limit (° C.) | Lower Limit (° C.) |
| Liquid Crystal Element 1 | 50.2 | 42.4 | 56.8 | <0° C. |
| Liquid Crystal Element 2 | 49.6 | 41.8 | 65.2 | <0° C. |
| Liquid Crystal Element 3 | 50.2 | 41.7 | 59.3 | <0° C. |
| Liquid Crystal Element 4 | 49.0 | 39.1 | 58.9 | <0° C. |
| Liquid Crystal Element 5 | 51.1 | 44.3 | 62.4 | <0° C. |
| Comparative Liquid Crystal Element | 34.0 | 26.3 | 42.5 | 3.3° C. |

Liquid Crystal Element 1 prior to the polymer stabilization treatment exhibited a blue phase within a temperature range, the upper limit of which was 50.2° C. and the lower limit of which was 42.4° C. However, Liquid Crystal Element 1 subsequent to the polymer stabilization treatment exhibited a blue phase within a temperature range, the upper limit of which was increased to 56.8° C., and a blue phase was also observed even at 0° C.

Liquid Crystal Element 2 prior to the polymer stabilization treatment exhibited a blue phase within a temperature range, the upper limit of which was 49.6° C. and the lower limit of which was 41.8° C. However, Liquid Crystal Element 2 subsequent to the polymer stabilization treatment exhibited a blue phase within a temperature range, the upper limit of which was increased to 65.2° C., and a blue phase was also observed even at 0° C.

Liquid Crystal Element 3 prior to the polymer stabilization treatment exhibited a blue phase within a temperature range, the upper limit of which was 50.2° C. and the lower limit of which was 41.7° C. However, Liquid Crystal Element 1 subsequent to the polymer stabilization treatment exhibited a blue phase within a temperature range, the upper limit of which was increased to 59.3° C., and a blue phase was also observed even at 0° C.

Liquid Crystal Element 4 prior to the polymer stabilization treatment exhibited a blue phase within a temperature range, the upper limit of which was 49.0° C. and the lower limit of which was 39.1° C. However, Liquid Crystal Element 4 subsequent to the polymer stabilization treatment exhibited a blue phase within a temperature range, the upper limit of which was increased to 58.9° C., and a blue phase was also observed even at 0° C.

Liquid Crystal Element 5 prior to the polymer stabilization treatment exhibited a blue phase within a temperature range, the upper limit of which was 51.1° C. and the lower limit of which was 44.3° C. However, Liquid Crystal Element 5 subsequent to the polymer stabilization treatment exhibited a blue phase within a temperature range, the upper limit of which was increased to 62.4° C., and a blue phase was also observed even at 0° C.

Therefore, as for Liquid Crystal Elements 1 to 5, it was confirmed that the temperature range where a blue phase was exhibited was able to be greatly widened by the polymer stabilization treatment.

On the other hand, the comparative liquid crystal element prior to the polymer stabilization treatment exhibited a blue phase within a temperature range, the upper limit of which was 34.0° C. and the lower limit of which was 26.3° C. The comparative liquid crystal element subsequent to the polymer stabilization treatment exhibited a blue phase within a temperature range, the lower limit of which was 3.3° C., i.e., higher than 0° C., and the upper limit of which was 42.5° C., which was not increased so much. Thus, the temperature range where a blue phase was exhibited was not widened as compared to that of Liquid Crystal Elements 1 to 5.

Therefore, it is shown that the liquid crystal element including the novel liquid crystalline compound described in this example, which is one embodiment of the present invention, exhibits a blue phase within a wider temperature range than a conventional liquid crystal element.

Further, voltage was applied to Liquid Crystal Elements 1 to 5 and the comparative liquid crystal element, and the transmittance and the contrast with respect to an applied voltage were evaluated. The characteristic evaluation was performed with a liquid crystal evaluation system (LCD-7200 produced by Otsuka Electronics Co., Ltd.) under the following conditions. A halogen lamp was used as a light source; and the temperature was set to room temperature. Liquid Crystal Elements 1 to 5 and the comparative liquid crystal element were sandwiched between polarizers in crossed nicols.

Figure 6:
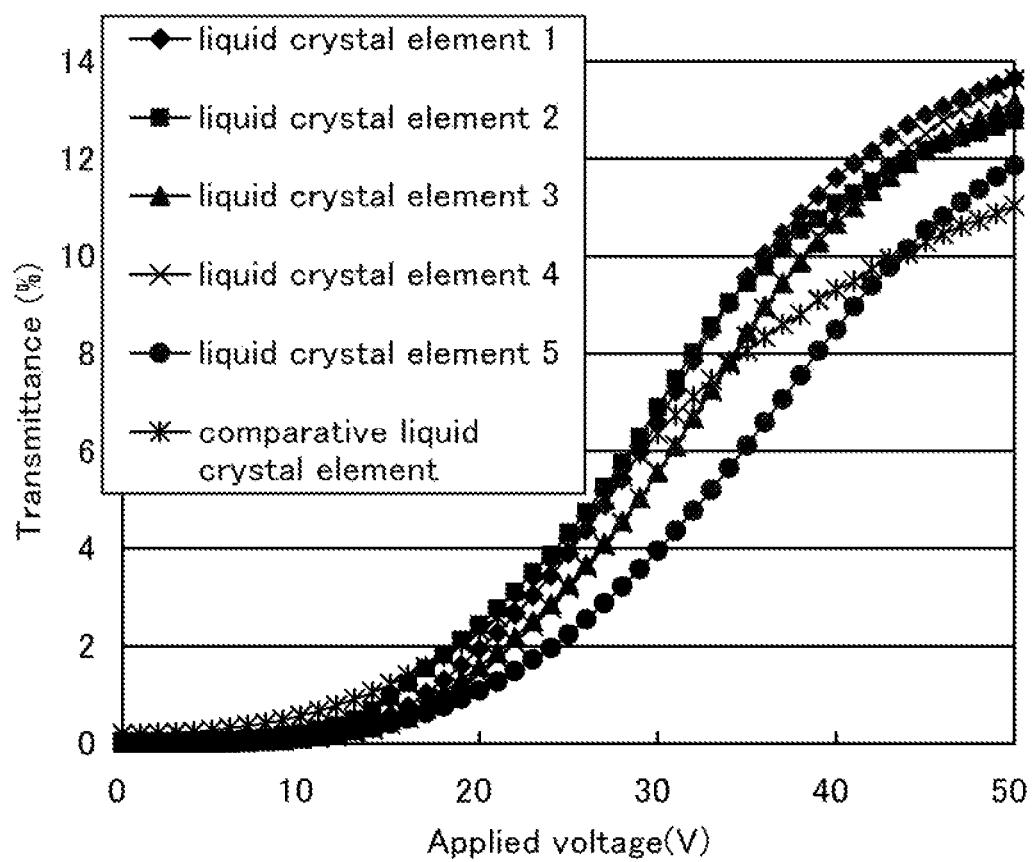
FIG. 6 is a graph showing a relation between applied voltage and transmittance of Liquid Crystal Elements 1 to 5 and a comparative liquid crystal element.
Figure 7:
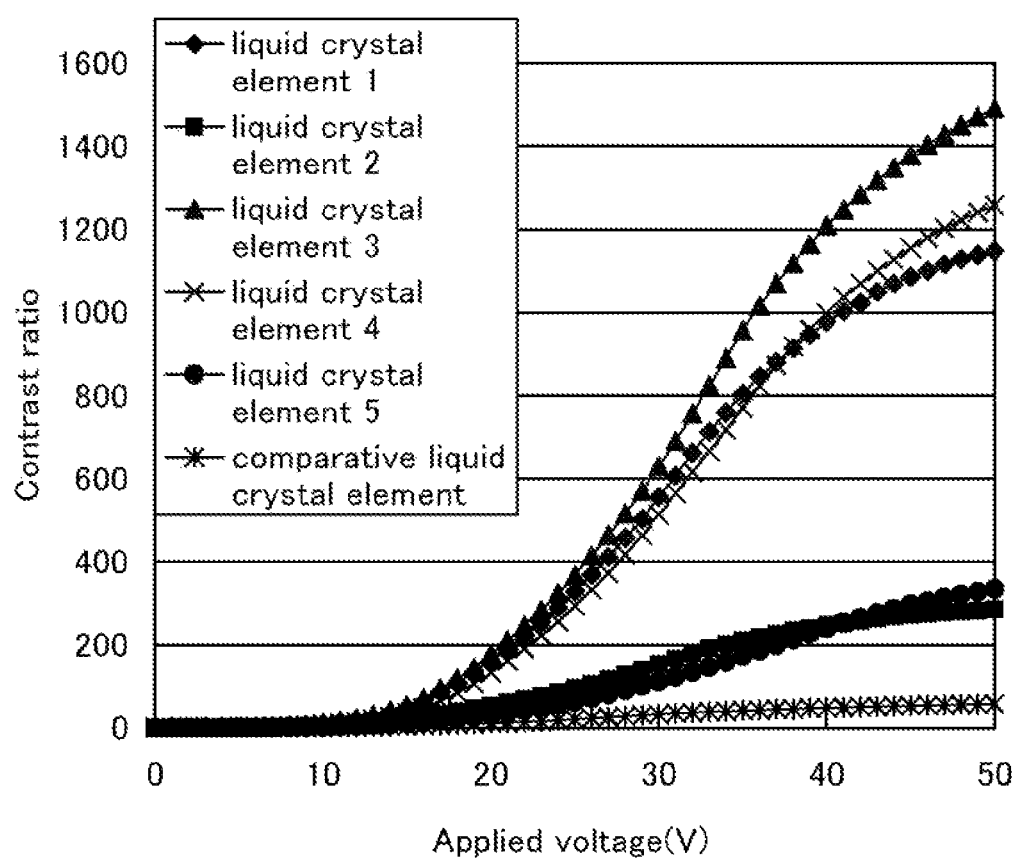
FIG. 7 is a graph showing a relation between applied voltage and contrast ratio of Liquid Crystal. Elements 1 to 5 and the comparative liquid crystal element.

FIG. 6 shows the relation between the applied voltage and the transmittance of Liquid Crystal Elements 1 to 5 and the comparative liquid crystal element. FIG. 7 shows the relation between the applied voltage and the contrast ratio of Liquid Crystal Elements 1 to 5 and the comparative liquid crystal element. The contrast ratio with respect to the applied voltage in FIG. 7 was calculated from the transmittance in FIG. 6. Specifically, the contrast ratio at an applied voltage of 0 V was set to 1, and the transmittance at each applied voltage was divided by the transmittance at an applied voltage of 0 V. In this manner, the contrast ratio was calculated. Note that in FIG. 6 and FIG. 7, characteristics of Liquid Crystal Element 1 are represented by rhombus data markers, characteristics of Liquid Crystal Element 2 are represented by square data markers, characteristics of Liquid Crystal Element 3 are represented by triangle data markers, characteristics of Liquid Crystal Element 4 are represented by x-shaped data markers, characteristics of Liquid Crystal Element 5 are represented by circular data markers, and characteristics of comparative liquid crystal element are represented by asterisk data markers.

As shown in FIG. 6, when the applied voltage is particularly high, the transmittance of Liquid Crystal Elements 1 to 5 with respect to the applied voltage is higher than that of the comparative liquid crystal element. Further, the transmittance at an applied voltage of 0 V of Liquid Crystal Elements 1 to 5 is lower than that of the comparative liquid crystal element. The difference between Liquid Crystal Elements 1 to 5 and the comparative liquid crystal element is remarkable in the contrast ratio of FIG. 7. At the same applied voltage, the contrast ratio of Liquid Crystal Elements 1 to 5 is higher than that of the comparative liquid crystal element.

As described above, it can be confirmed that a liquid crystal composition including the novel liquid crystalline compound of this example has a wide temperature range where a blue phase is exhibited.

Further, a liquid crystal element including the liquid crystal composition including the novel liquid crystalline compound of this example has high contrast, and thus, a liquid crystal display device including the liquid crystal element can provide high contrast.

EXPLANATION OF REFERENCE

200: first substrate, 201: second substrate, 202*a*: alignment film, 202*b*: alignment film, 208: liquid crystal composition, 230: pixel electrode layer, 232: common electrode layer, 401: gate electrode layer, 402: gate insulating layer, 403: semiconductor layer, 405*a*: wiring layer, 405*b*: wiring layer, 407: insulating film, 408: common wiring layer, 409: insulating film, 413: interlayer film, 420: transistor, 441: first substrate, 442: second substrate, 443*a*: polarizing plate, 443*b*: polarizing plate, 444: liquid crystal composition, 446: electrode layer, 446*a*: electrode layer, 446*b*: electrode layer, 446*c*: electrode layer, 446*d*: electrode layer, 447: electrode layer, 447*a*: electrode layer, 447*b*: electrode layer, 447*c*: electrode layer, 447*d*: electrode layer, 2701: housing, 2703: housing, 2705: display portion, 2707: display portion, 2711: hinge, 2721: power switch, 2723: operation key, 2725: speaker, 2800: housing, 2801: housing, 2802: display panel, 2803: speaker, 2804: microphone, 2805: operation key, 2806: pointing device, 2807: camera lens, 2808: external connection terminal, 2810: solar cell, 2811: external memory slot, 3001: main body, 3002: housing, 3003: display portion, 3004: keyboard, 3021: main body, 3022: stylus, 3023: display portion, 3024: operation button, 3025: external interface, 3051: main body, 3053: eyepiece, 3054: operation switch, 3056: battery, 4001: first substrate, 4002: pixel portion, 4003: signal line driver circuit, 4003*a*: signal line driver circuit, 4003*b*: signal line driver circuit, 4004: scanning line driver circuit, 4005: sealant, 4006: second substrate, 4008: liquid crystal composition, 4010: transistor, 4011: transistor, 4013: liquid crystal element, 4015: connection terminal electrode, 4016: terminal electrode, 4019: anisotropic conductive film, 4020: insulating layer, 4021: interlayer film, 4030: pixel electrode layer, 4031: common electrode layer, 4032*a*: polarizing plate, 4032*b*: polarizing plate, 4034: light-blocking layer, 9601: housing, 9603: display portion, and 9605: stand This application is based on Japanese Patent Application serial no. 2011-018032 filed with Japan Patent Office on Jan. 31, 2011, the entire contents of which are hereby incorporated by reference.

The invention claimed is:

1. A liquid crystalline compound represented by a general formula (G1):

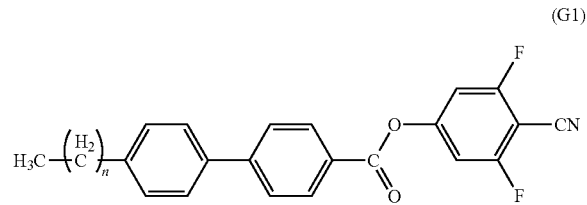

(G1)

wherein n is an integer of 2 to 10, and
wherein n is an even number other than 4.

2. The liquid crystalline compound according to claim 1, wherein n is an integer of 6 to 10.

3. A liquid crystal composition comprising a liquid crystalline compound represented by a general formula (G1):

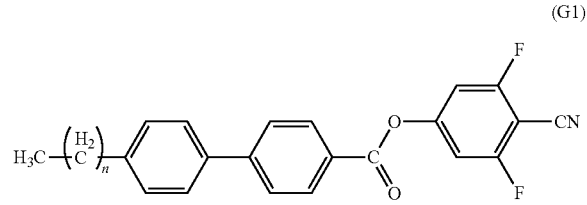

(G1)

wherein n is an integer of 2 to 10, and
wherein n is an even number other than 4.

4. The liquid crystal composition according to claim 3, wherein n is an integer of 6 to 10.

5. The liquid crystal composition according to claim 3, further comprising at least one of a liquid crystalline compound, a non liquid crystalline compound, and a chiral agent.

6. The liquid crystal composition according to claim 3, further comprising a plurality of liquid crystalline compounds,
wherein a ratio of the liquid crystalline compound represented by the general formula (G1) to a sum of the liquid crystalline compound represented by the general formula (G1) and the plurality of liquid crystalline compounds is the lowest.

7. A liquid crystal element comprising a material based on a composition including a liquid crystalline compound represented by a general formula (G1):

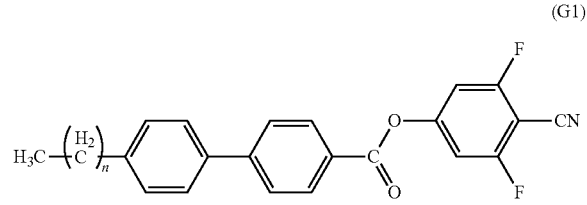

(G1)

wherein n is an integer of 2 to 10, and
wherein n is an even number other than 4.

8. The liquid crystal element according to claim 7, wherein n is an integer of 6 to 10.

9. The liquid crystal element according to claim 7, wherein the liquid crystal element is capable of exhibiting a blue phase.

10. The liquid crystal element according to claim 7, wherein the liquid crystal element is capable of exhibiting a blue phase at 0° C.

11. A liquid crystal display device comprising the liquid crystal element according to claim 7.

12. The liquid crystal display device according to claim 11, further comprising:
a first substrate;
a first electrode over the first substrate;
a second electrode over the first substrate;
a liquid crystal layer over the first electrode and the second electrode, the liquid crystal layer including the liquid crystalline compound; and
a second substrate over the liquid crystal layer,
wherein the liquid crystal layer is interposed between the first substrate and the second substrate.

13. The liquid crystal display device according to claim 12, wherein the first electrode is provided over the second electrode.

* * * * *

UNITED STATES PATENT AND TRADEMARK OFFICE
CERTIFICATE OF CORRECTION

PATENT NO.       : 8,603,595 B2
APPLICATION NO.  : 13/358740
DATED            : December 10, 2013
INVENTOR(S)      : Sachiko Kawakami et al.

It is certified that error appears in the above-identified patent and that said Letters Patent is hereby corrected as shown below:

In the Specification:

Column 2, line 61, "being, limited" should read "being limited"

Column 4, line 17, "3,5-di Fluorophenyl" should read "3,5-difluorophenyl"

Column 4, line 24, "3,5-d fluorophenyl" should read "3,5-difluorophenyl"

Column 7, line 58, "compound, (PPEP-" should read "compound (PPEP-"

Column 8, line 9, "(11 is" should read "(n is"

Column 8, line 61, "structure; and" should read "structure, and"

Column 11, line 63, "using, one" should read "using one"

Column 13, line 3, "siring layer" should read "wiring layer"

Column 15, line 6, "resin, is, preferably" should read "resin is preferably"

Column 15, line 60, "plates in consideration" should read "plates. In consideration"

Column 15, line 63, "preferable: that" should read "preferable that"

Column 16, line 17, "(Cu) and" should read "(Cu), and"

Column 16, line 54, "structure," should read "structure"

Column 17, line 7, "siloxane, (OMCTS)" should read "siloxane (OMCTS)"

Column 20, line 12, "portion 4092" should read "portion 4002"

Column 20, line 20, "Mounted" should read "mounted"

Column 22, line 7, "organic, substance" should read "organic substance"

Column 22, line 8, "air and, is" should read "air and is"

Column 22, line 11, "silicon, oxynitride film" should read "silicon oxynitride film"

Column 23, line 7, "embodiment: of" should read "embodiment of"

Column 23, line 12, "As above" should read "As described above"

Signed and Sealed this
Fifteenth Day of April, 2014

Michelle K. Lee
*Deputy Director of the United States Patent and Trademark Office*

CERTIFICATE OF CORRECTION (continued)
U.S. Pat. No. 8,603,595 B2

In the Specification:

Column 24, line 37, "is, incorporated" should read "is incorporated"

Column 24, line 62, "data, can" should read "data can"

Column 25, line 21, "modern" should read "modem"

Column 26, line 32, "8.18 (d, 21-1)" should read "8.18 (d, 2H)"

Column 26, line 44, "described:" should read "described."

Column 27, line 12, "1.3 (8.4 mmol)" should read "1.3 g (8.4 mmol)"

Column 27, line 44, "(On, 4H)" should read "(m, 4H)"

Column 28, line 34, "were, combined" should read "were combined"

Column 28, line 35, "saline;" should read "saline,"

Column 29, line 2, "3,5-di fluorophenyl" should read "3,5-difluorophenyl"

Column 30, line 7, "2.07 (t," should read "2.67 (t,"

Column 33, line 20, "CPP-3 FF" should read "CPP-3FF"

Column 34, line 7, "Chemical industry" should read "Chemical Industry"

Column 36, line 61, "temperature, was" should read "temperature was"

Column 37, line 17, "liquid, crystal" should read "liquid crystal"

Column 38, line 54, "source; and" should read "source, and"

Column 39, line 39, "of comparative" should read "of the comparative"